(12) United States Patent
Smith

(10) Patent No.: US 12,105,076 B2
(45) Date of Patent: Oct. 1, 2024

(54) CARBONATE GRAIN COARSENESS ANALYSIS AND RELATED METHODS

(71) Applicant: Michael P. Smith, Tulsa, OK (US)

(72) Inventor: Michael P. Smith, Tulsa, OK (US)

(*) Notice: Subject to any disclaimer, the term of this patent is extended or adjusted under 35 U.S.C. 154(b) by 755 days.

(21) Appl. No.: 17/194,194

(22) Filed: Mar. 5, 2021

(65) Prior Publication Data

US 2021/0215652 A1 Jul. 15, 2021

Related U.S. Application Data

(63) Continuation-in-part of application No. PCT/US2019/049613, filed on Sep. 5, 2019.

(60) Provisional application No. 62/727,530, filed on Sep. 5, 2018.

(51) Int. Cl.
    *G01N 33/24* (2006.01)
    *E21B 49/02* (2006.01)
    *G01N 33/00* (2006.01)

(52) U.S. Cl.
    CPC ............ *G01N 33/24* (2013.01); *E21B 49/02* (2013.01); *G01N 33/004* (2013.01)

(58) Field of Classification Search
    CPC .... G01N 33/24; G01N 33/241; G01N 33/004; E21B 49/02–06
    See application file for complete search history.

(56) References Cited

U.S. PATENT DOCUMENTS

| 4,495,414 A | 1/1985 | Barrie |
| 4,525,328 A | 6/1985 | Bredeweg |
| 4,797,906 A | 1/1989 | Smith |
| 4,960,567 A | 10/1990 | Smith |

(Continued)

FOREIGN PATENT DOCUMENTS

| BR | 1120190119442 | 4/2023 |
| CA | 2068012 | 12/1992 |

(Continued)

OTHER PUBLICATIONS

Machine translation of WO 2015/092247 A1 (Year: 2015).*

(Continued)

*Primary Examiner* — Judy Nguyen
*Assistant Examiner* — James Split
(74) *Attorney, Agent, or Firm* — Len S. Smth; Transformative Legal, LLC

(57) ABSTRACT

Provided herein are methods of characterizing rock qualities, such qualities of rock obtained as cuttings from petroleum operations. One embodiment comprises determining the carbonate grain size of one or more rock samples by subjecting the samples to conditions that cause release of carbon dioxide or carbon dioxide-related compound(s) and quantifying the amount thereof. In another embodiment, the invention provides a method of identifying regions of a geologic area likely to be associated with faults by identifying regions of low carbon dioxide or other target volatile compound(s) compared with expected properties and/or the surroundings of the low volatile compound region. Other methods involve analyzing differences in the amounts of compounds of different sizes in different geologic areas. The methods can aid in guiding petroleum exploration and/or production operations.

16 Claims, 7 Drawing Sheets

(56) References Cited

U.S. PATENT DOCUMENTS

| | | | |
|---|---|---|---|
| 5,241,859 | A | 9/1993 | Smith |
| 5,286,651 | A | 2/1994 | Smith |
| 5,328,849 | A | 7/1994 | Smith |
| 5,341,859 | A | 8/1994 | Howseman, Jr. |
| 5,411,707 | A | 5/1995 | Hiatt |
| 5,416,024 | A | 5/1995 | Smith |
| 5,447,556 | A | 9/1995 | Pleil |
| 5,457,316 | A | 10/1995 | Cohen |
| 5,767,399 | A | 6/1998 | Smith |
| 6,511,707 | B1 | 1/2003 | MacDonald |
| 6,541,272 | B1 | 4/2003 | Mitra |
| 6,661,000 | B2 | 12/2003 | Smith |
| 6,743,397 | B1 | 6/2004 | Zesiger |
| 7,210,342 | B1 | 5/2007 | Sterner et al. |
| 7,395,691 | B2 | 7/2008 | Sterner |
| 8,256,282 | B2 | 9/2012 | Schlachter |
| 8,536,524 | B2 | 9/2013 | Pomerantz |
| 10,190,413 | B2 | 1/2019 | Smith |
| 10,260,336 | B2 | 4/2019 | Smith |
| 10,494,919 | B2 | 12/2019 | Smith |
| 2001/0015093 | A1 | 8/2001 | Kempe |
| 2002/0194896 | A1 | 12/2002 | Stolper |
| 2004/0099804 | A1 | 5/2004 | Liu et al. |
| 2005/0109207 | A1 | 5/2005 | Olander |
| 2005/0194134 | A1 | 9/2005 | McGregor |
| 2010/0277724 | A1 | 11/2010 | Bounouar |
| 2011/0305309 | A1 | 12/2011 | Brown |
| 2012/0167786 | A1 | 7/2012 | Laugharn, Jr. |
| 2012/0186331 | A1 | 7/2012 | Tipler |
| 2014/0026638 | A1 | 1/2014 | Bowers, II |
| 2014/0220700 | A1 | 8/2014 | Alexander |
| 2014/0283580 | A1 | 9/2014 | Rouchon |
| 2015/0123670 | A1 | 5/2015 | Robbat, Jr |
| 2015/0155150 | A1 | 6/2015 | Bateman |
| 2015/0167052 | A1 | 6/2015 | Griffin |
| 2015/0346179 | A1 | 12/2015 | Pillot |
| 2016/0222781 | A1 | 8/2016 | Lawson |
| 2018/0195383 | A1 | 7/2018 | Smith |
| 2020/0408732 | A1 | 12/2020 | Smith |

FOREIGN PATENT DOCUMENTS

| | | |
|---|---|---|
| CN | 1609586 A | 4/2005 |
| CN | 201740685 U | 2/2011 |
| CN | 2017080246 | 3/2011 |
| CN | 104407089 A | 3/2015 |
| EP | 0414564 A2 | 2/1991 |
| EP | 0414564 B1 | 10/1995 |
| FR | 2972803 | 9/2012 |
| WO | WO2003050844 A1 | 6/2003 |
| WO | WO-2012127130 A1 * | 9/2012 ........... G01N 33/241 |
| WO | WO2015050832 A1 | 4/2015 |
| WO | 2015092247 | 6/2015 |
| WO | WO2016186689 A1 | 11/2016 |
| WO | 2018111945 | 6/2018 |
| WO | 2020051259 | 3/2020 |

OTHER PUBLICATIONS

Madkour et al., "Environmental texture and geochemistry of the sediments of a subtropical mangrove ecosystem and surrounding areas, Red Sea Coast, Egypt," Arabian Journal of Geosciences, vol. 7, No. 9, pp. 3427-3440 (Year: 2014).*
Jones, et al, Light hydrocarbons for Petroleum and Gas Prospecting:, 1999, Elsevier Science B.V.; p. 6.
Sugisaki, et al, "Origin of Hydrogen and Carbon Dioxide in the Fault Gases and its Relation to Fault Activity", May 1982, The Journal of Geology; Abstract.
International Search Report based on PCT/US2019/49613 filed Sep. 5, 2019, dated Nov. 13, 2019.
Jorge, et al., "Analysis of Volatiles in Fluid Inclusions by Direct online Crushing Mass Spectrometry", Journal of Brazilian Chemical Society, 22.3, 2011; 437-455, p. 445, col. 1 [online] URL<http://www.scielo.br/pdf/jbchs/v22n3/v22n3a05.pdf>.
McCarthy, Kevin et al., "Basic Petroleum Geochemistry for Source Rock Evaluation", Oilfield Review, 23.2, 2011.
International Search and Written Opinion for PCT/US2019/22362 filed Mar. 14, 2019, dated Aug. 5, 2019.
Non-Final Office Action on May 17, 2018 for U.S. Appl. No. 15/908,760, Campbell, Irving A.
Extended European Search Report on Jul. 30, 2020 for EP178808861.
Indian Examination Report on May 16, 2021 for IN2019170221802.
International Search Report on Apr. 6, 2018 for PCT/US2017/065921.
Mazidi et al. "Measurement of Uniaxial Compressive Strength of Rocks Using Reconstructed Cores from Rock Cuttings." Journal of Petroleum Science and Engineering 86-87 (Mar. 26, 2012): 39-43, Mazidi, Sabor.
Non-Final Office Action on Oct. 9, 2018 for U.S. Appl. No. 16/019,523. Megna Fuentes, Anthony W.
Final Office Action on May 2, 2019 for U.S. Appl. No. 16/019,523, Megna Fuentes, Anthony W.
European Examination Report on Feb. 24, 2023 for EP178808861.
Russian Office Action on Aug. 19, 2020 for EA201991461.
Non-Final Office Action on Oct. 9, 2018 for U.S. Appl. No. 16/019,529, Wecker, Jennifer.

* cited by examiner

FIG. 2A
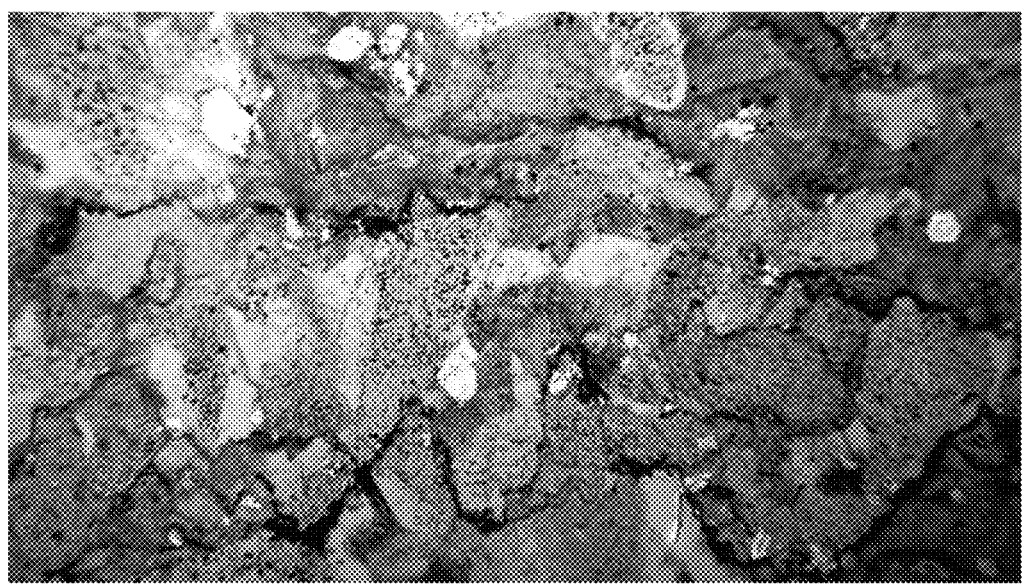
FIG. 2B
FIG. 2

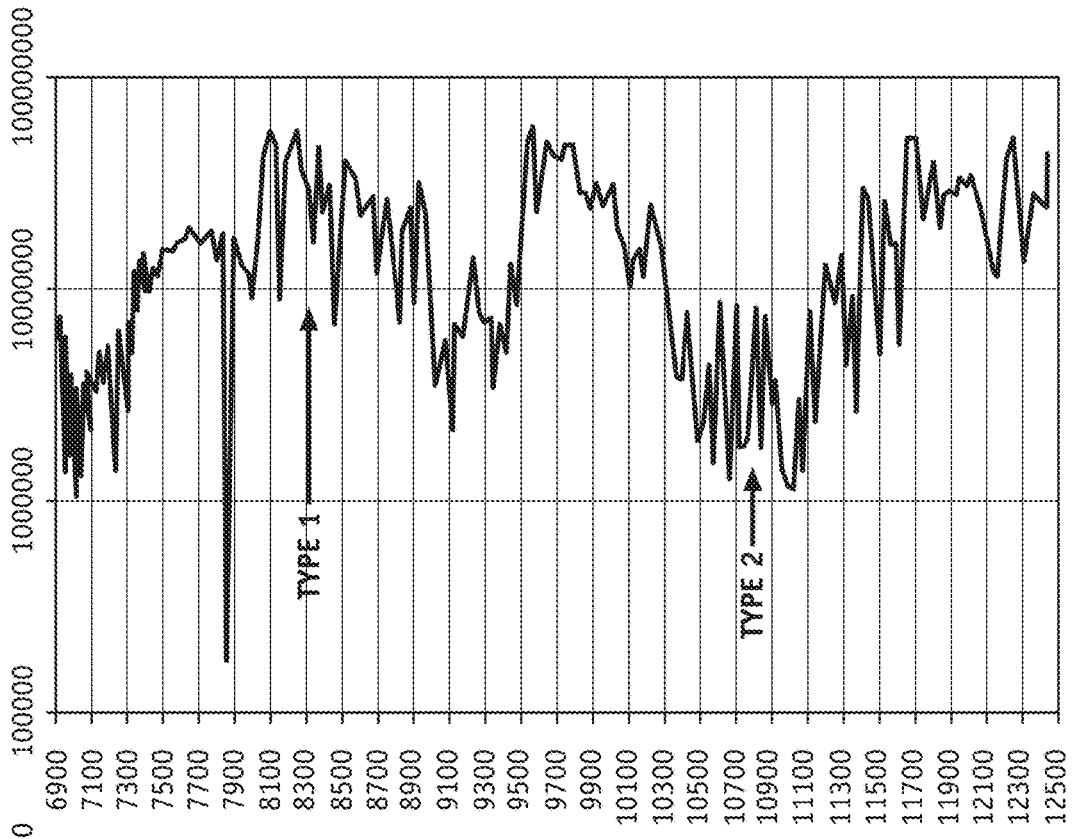
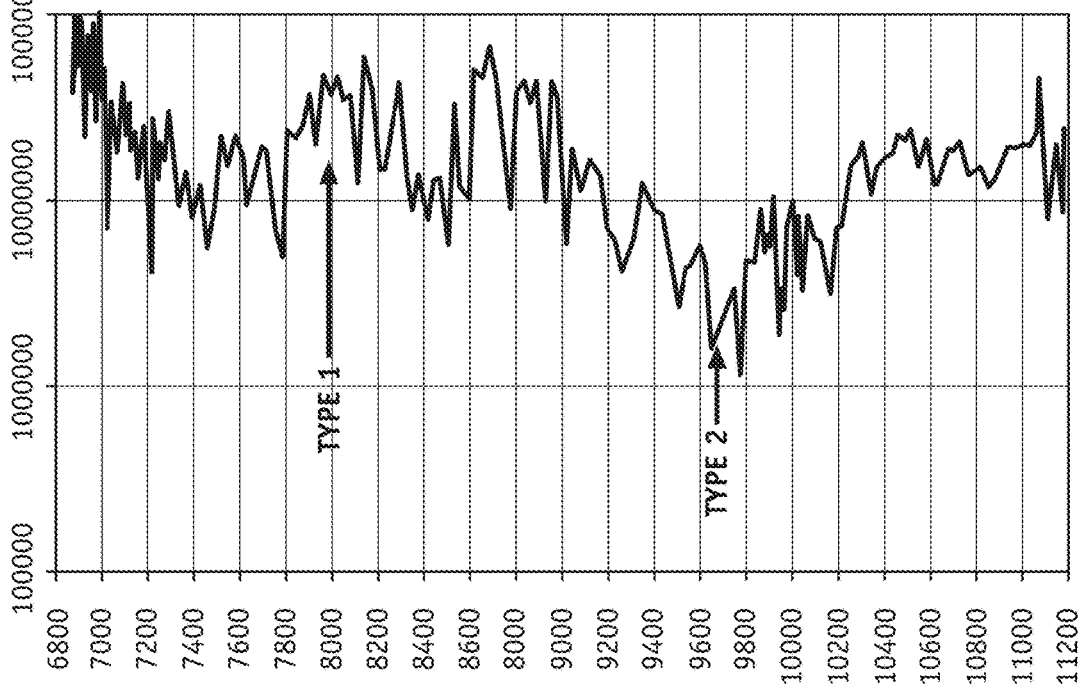
FIG. 3A
FIG. 3B
FIG. 3

| U.S. standard sieve mesh | Millimeters | Phi (φ) units | Wentworth size class | |
|---|---|---|---|---|
| | | 4096 | -12 | |
| | | 1024 | -10 | Boulder |
| GRAVEL | | 256 | 256 | -8 |
| | | 64 | 64 | -6 | Cobble |
| | | 16 | | -4 | Pebble |
| | 5 | 4 | 4 | -2 | |
| | 6 | 3.36 | | -1.75 | |
| | 7 | 2.83 | | -1.5 | Granule |
| | 8 | 2.38 | | -1.25 | |
| | 10 | 2.00 | 2 | -1.0 | |
| | 12 | 1.68 | | -0.75 | |
| | 14 | 1.41 | | -0.5 | Very coarse sand |
| | 16 | 1.19 | | -0.25 | |
| | 18 | 1.00 | 1 | 0.0 | |
| | 20 | 0.84 | | 0.25 | |
| | 25 | 0.71 | | 0.5 | Coarse sand |
| | 30 | 0.59 | | 0.75 | |
| SAND | 35 | 0.50 | ½ | 1.0 | |
| | 40 | 0.42 | | 1.25 | |
| | 45 | 0.35 | | 1.5 | Medium sand |
| | 50 | 0.30 | | 1.75 | |
| | 60 | 0.25 | ¼ | 2.0 | |
| | 70 | 0.210 | | 2.25 | |
| | 80 | 0.177 | | 2.5 | Fine sand |
| | 100 | 0.149 | | 2.75 | |
| | 120 | 0.125 | ⅛ | 3.0 | |
| | 140 | 0.105 | | 3.25 | |
| | 170 | 0.088 | | 3.5 | Very fine sand |
| | 200 | 0.074 | | 3.75 | |
| | 230 | 0.0625 | 1/16 | 4.0 | |
| | 270 | 0.053 | | 4.25 | |
| | 325 | 0.044 | | 4.5 | Coarse silt |
| | | 0.037 | | 4.75 | |
| MUD | SILT | 0.031 | 1/32 | 5.0 | |
| | | 0.0156 | 1/64 | 6.0 | Medium silt |
| | | 0.0078 | 1/128 | 7.0 | Fine silt |
| | | 0.0039 | 1/256 | 8.0 | Very fine silt |
| | | 0.0020 | | 9.0 | |
| | | 0.00098 | | 10.0 | Clay |
| | CLAY | 0.00049 | | 11.0 | |
| | | 0.00024 | | 12.0 | |
| | | 0.00012 | | 13.0 | |
| | | 0.00006 | | 14.0 | |

FIG. 7

CARBONATE GRAIN COARSENESS ANALYSIS AND RELATED METHODS

CROSS-REFERENCE TO RELATED APPLICATIONS

This Application is a continuation-in-part of presently International Patent Application PCT/US2019/49613, which designates the United States, filed Sep. 5, 2019, which claims the benefit of priority to U.S. Provisional Patent Application 62/727,530, filed Sep. 5, 2018, both of which are incorporated by reference in its entirety herein.

FIELD OF THE INVENTION

The inventions described herein relate to the characterization of rocks and geologic formations, such as certain types of rock, e.g., carbonate rock, and/or geologic areas/sites (e.g., petroleum wells or areas associated with petroleum production/exploration), including larger geologic units such as formations associated with petroleum exploration and production.

BACKGROUND OF THE INVENTION

It is valuable in petroleum exploration and production and in other ventures that extract mineral wealth from the earth, dispose of waste in the earth, or that utilize rocks or materials derived from rocks, to understand the nature of the rocks or rock-derived materials. Such information can be especially helpful when information obtained from analyzing rocks can be used in connection with a related material (e.g., oil exploration) or activity associated with rocks. A number of currently expensive technologies are available for evaluating various properties of rocks, including, but not limited to, core sampling (or "coring"), using both conventional and side wall cores, and a number of other real time and wire line logging tools known in the mineral and petroleum exploration fields.

One of the most commonly used methods of evaluating rock quality in a petroleum well is the gamma ray log. In most oil and gas wells, gamma rays are primarily produced by the elements potassium (K), uranium (U), and thorium (Th). For the most part these elements are most commonly found in clays that constitute much of the minerals in shale. Shale, therefore, typically emits high amounts of gamma rays relative to other rocks. Other sedimentary rocks, in particular sandstones and carbonates are clay poor relative to shales, and hence emit low amounts of gamma rays.

Sedimentary rocks can be broadly divided into two categories: clastics and carbonates, although there is some overlap. Clastic sediments primarily belong to the family of sandstones, siltstones, and shales, ordered in decreasing grain size and increasing clay content. A "clast" is a fragment of rock or mineral, ranging in size from less than a micron to larger than a typical home, and clastic rocks are composed of such rocks or minerals. Generally speaking, with decreasing grain size clay content increases. This is a reflection of the energy of the depositional environment. Clean sands, for example, are deposited by rapid moving water in streams, rivers, and oceans. Mud stones are deposited in more still water from these same environments. Siltstones form somewhere in between these two energy extremes.

In clastic rocks ("clastics") gamma ray logs can be used to map clean coarse sandstones, versus more clay-rich, finer-grained siltstones, versus very fine-grained shales and mudstones. Sandstones have low gamma ray emissions; siltstones have higher gamma emissions; and shales have gamma emissions that are higher yet. From the gamma ray log, one can evaluate, e.g., where the best clastic reservoir rock may be located (in petroleum production), and where the best seal and source rocks and unconventional petroleum targets may occur. Coarsening upward and fining upward sequences characteristic of marine versus meandering stream environments can be documented. In clastics, the gamma ray log is invaluable.

Carbonates, however, are chemical sediments formed from the shells of marine animals (limestone, for example, is a common type of a carbonate). Generally, carbonates are comprised mostly of calcite and/or dolomite, neither of which contain any appreciable amounts of K, U, or Th. Thus, for the most part, carbonates are not usually distinguishable one from another using a gamma ray log. This is unfortunate as carbonates, just like clastics, can either be coarse or fine grained, or somewhere in the middle. However, also unlike clastics, carbonate grain sizes cannot be readily determined using X-ray Fluorescence analysis and X-ray diffraction techniques. Techniques such as those described in, e.g., PCT patent publication WO2015/092247 to Lozach and CN201780246 to Yu, et. al. provide mechanisms for determining the carbonate grain content of a rock or rock sample, whereby, for example, chemical disruption or thermal decomposition is utilized to release $CO_2$ which is then measured. However, these techniques cause the release of $CO_2$ present as a structural component of carbonate mineral grains (in the form of the $CO_3^{2-}$ ion). Thus, while such techniques may be helpful in determining the type of rock analyzed, e.g., identifying that a rock is a carbonate rock, such techniques provide no insight into the size of carbonate grains present within an identified carbonate rock (and categorizing carbonate rock coarseness).

The texture of carbonate rocks, including the size of the grains that compose these rocks, are important in oil and gas exploration and production, as well as in other economic and environmental endeavors, as the textures and fabrics of clastic rocks. Accordingly, there is a need for methods to analyze the grain size of such carbonate rocks rapidly and economically, especially in the context of industrial applications that are dependent on drilling or mining, such as petroleum exploration and production. This need is particularly critical for petroleum drill cuttings, especially polycrystalline diamond (PCD) bit drill cuttings, in which the small size of the individual cuttings pieces makes visual and other grain size determinations difficult or impossible.

It is understood in the geological arts that the grain size of carbonates often corresponds to the size of fluid inclusions contained in such rocks. Methods of performing fluid inclusion analysis are well known and have been performed for years.

U.S. Pat. No. 4,960,567, for example, relates to one of my prior inventions, namely a method for obtaining gasses from fluid inclusions for analysis through mass spectrometry; and U.S. Pat. No. 5,241,859, similarly relates to one of my prior inventions and provides a method in which material from a collection of fluid inclusions are analyzed to identify collections that are rich in hydrocarbons, which can then be further analyzed, such as through mass spectrometry analysis. Likewise, U.S. Pat. No. 5,328,849 describes methods for mapping subsurface formations by analyzing fluid inclusions in several samples through specialized devices I also previously invented.

Fluid inclusions are not the only components of rocks that may be relevant to geological analysis. For example, U.S.

Pat. No. 6,661,000 describes an invention made by me and my co-inventors wherein we invented a method for analyzing surface and pore liquids, as opposed to fluid inclusions, by a method in which cuttings or other samples are subjected directly to mass spectrometry analysis under high vacuum. However, a shortcoming with that method is the loss of gasses associated with the sample due to the need to apply such relatively high vacuum levels in order to make the devices we invented operate.

Rock volatiles stratigraphy ("RVS") is a new technology/field of analysis that I have invented and that allows for improved analysis of rocks, such as petroleum drilling cuttings, to determine the properties of a geological area, such as a petroleum exploration or production site. Although RVS can be practiced in several different ways, the primary application of the RVS method is through subjecting samples to a cryogenic mass spectrometry method of capturing volatile compounds released from rock samples with a cryogenic trap, selectively releasing the volatile compounds from the trap, and analyzing the compounds through mass spectrometry. RVS methods are described in detail in U.S. Provisional Application No. 62/434,399, filed Dec. 14, 2016, International Patent Application PCT/US2017/065921, filed Dec. 12, 2017, U.S. Provisional Application No. 62/634,794, filed Feb. 23, 2018, and U.S. Provisional Application No. 62/643,132, filed Mar. 14, 2018 (collectively, the "RVS applications"). Because the RVS applications and other patent documents cited here are relevant to the understanding and/or practice of the present invention, they are all specifically and especially incorporated herein in their entirety.

BRIEF DESCRIPTION OF THE DRAWINGS/FIGURES

FIG. 1 provides a graphical illustration demonstrating how different rock types are distinguishable via $CO_2$ analysis of cuttings obtained from a single petroleum well. FIG. 1 illustrates distinct $CO_2$ levels as measured by the current method (mass spec response, digitized voltage signal; top scale of graph) across the depth of the well (as measured in feet; side scale of graph). Differences in $CO_2$ content correlate with differences in grain size with higher $CO_2$ levels being measured in rock containing a higher grain size. FIG. 1 contains data from EXAMPLE 1.

FIG. 2 illustrates two types of rock distinguishable by the current invention.

FIG. 3 (including FIGS. 3A and 3B) provides graphs demonstrating distinction between the rock types, characterized as Type I and Type II rock in the exemplary embodiment of the present invention described in the Examples, as identified in multiple wells. Graphs of FIG. 3 demonstrate the applicability of the current invention to comparison of rock content across 2 (or more) wells. FIG. 3A illustrates Type I rock, with a higher $CO_2$ release, as indicted by higher mass spec response (top scale of graph) than that of Type 2 rock, located deeper in the well (side scale of graph, in feet). Type I and Type II rock, with their differing $CO_2$ content, indicate rock types with different grain size. FIG. 3B is a similar illustration, however rock Types I and II appear at differing well depths. Such well-to-well comparison provides supporting data for decisions related to pursuing one site over another.

FIG. 3A contains data from EXAMPLE 1. FIG. 3B contains data from EXAMPLE 2.

FIG. 4 illustrates the $CO_2$ analysis of cuttings from a single well in which very little $CO_2$ was detected, as discussed in the Examples. In shallow areas of the well, low amounts of $CO_2$ are detected. This lower $CO_2$ release is believed to be indicative of a partial fault which has induced $CO_2$ loss and therefore rocks characterized as Type I and Type II in the present invention are difficult to distinguish. In deeper areas of the well, extreme low $CO_2$ levels are measured. The lack of $CO_2$ indicates extensive grain fracturing and subsequent significant $CO_2$ loss at the site of a fault. FIG. 4 contains data from EXAMPLE 3.

FIG. 5 provides a graphical side-by-side comparison of data for various compounds measured between two wells, where in one part (FIG. 5A) the lack of $CO_2$ caused by the presence of faults makes the difference between rock Types I and II difficult to distinguish; and in the second part (FIG. 5B) the difference between rock Types I and II is distinguishable as $CO_2$ remains present as trapped within the varying grains of each type of rock and has not been released due to a fault or partial fault.

FIG. 7 is a chart providing the Wentworth grain-size scale for sediments, showing Wentworth size classes, equivalent phi ($\phi$) units, and sieve numbers of U.S. Standard Sieves corresponding to various millimeter and $\phi$ sizes, obtained from Boggs, "Principles of Sedimentology and Stratigraphy", Fourth Edition, Pearson Education, Inc., Upper Saddle River, NJ, ©2006, 2001, 1995.

SUMMARY OF THE INVENTION

Figure 1:
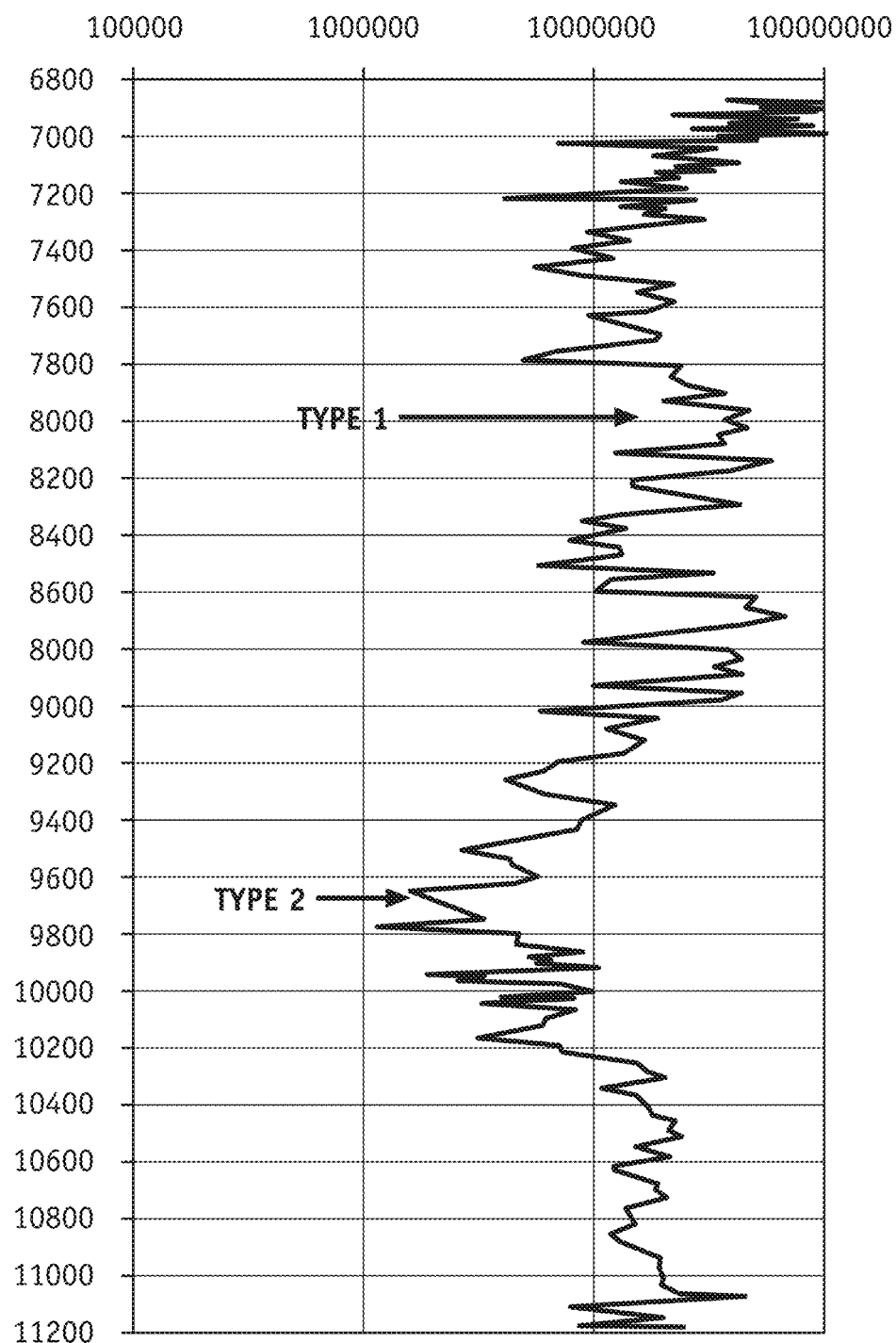

The invention described here provides, in one set of embodiments, new methods of identifying characteristics of carbonate rocks, including determining the grain size of carbonate rock. In aspects, such methods include measuring $CO_2$ and/or $CO_2$-related compounds associated with analyzed rocks. In aspects, methods relate to measuring the amount of $CO_2$ maintained within tight spaces of carbonate grains in samples as (1) $CO_2$ dissolved in water and/or oil, (2) as $CO_2$ gas, or (3) both. In aspects, such methods involve measuring very small (e.g., trace) amounts of carbon dioxide, as exemplified herein. In aspects, the methods herein primarily, essentially, or entirely do not rely on or do not include any analysis of $CO_2$ resulting from the breakdown of carbonate minerals, e.g., the decomposition of carbonate minerals, such that the methods do not analyze the $CO_2$ maintained within the crystalline structure of carbonate rock released only upon dissolution. In aspects, most, generally all (e.g., at least about 75%), substantially all (at least about 90%), essentially all, or all of the analyzed material/samples in the method are from rocks that are mostly, generally only, essentially only, or only composed of non-clastic rocks, are from material known to include a measurable amount of carbonate grains (e.g., are mostly composed of carbonate grains), or both. In aspects, most, generally all, substantially all, essentially all, or all samples/materialized analyzed are from rocks that exhibit a relatively consistent amount of carbon dioxide, carbon dioxide-related volatiles, or both (as compared to variability in presence/release of such compounds observed in most clastics, which can be highly variable). In aspects, most, generally all, substantially all, essentially all, or all samples/materials analyzed in the method comprise a detectable quantity/concentration of $CO_3^{2-}$ ions, e.g., in an amount typically present in carbonate grains in rocks categorized as carbonate rocks (while the presence of such ions can characterize materials, they are in many aspects not detected as part of the inventive method). In aspects, most, generally all, substantially all, essentially all, or all of the samples/materials analyzed are from a geologic site/area comprising subsurface fluids, wherein the amount of $CO_2$ dissolved in such subsurface fluid(s) is measurably or significantly limited by the thermodynamics of equilibrium between the fluid(s) and carbonate mineral structure of the material analyzed (or from which the samples analyzed are obtained). In aspects, less than about 33%, less than about 25%, less than about 15%, less than about 10%, less than about 5%, or less than about 1% of the rock(s) used as samples/material in methods is/are samples/material in which there is no measurable or significant thermodynamic limitation on the $CO_2$ content in site/area fluids, carbonate grains, or both.

In aspects, the methods described herein are utilized in the characterization of materials known to comprise, consist of, predominately comprise, consist essentially of, or be carbonate in nature. In aspects, the methods of the invention provide a tool for the characterization of grain size in carbonate rock, an analysis unavailable using conventional tools such as gamma ray logs. In aspects, the methods of characterizing carbonate rock characteristics, such as grain size, is determined at least partially without reference to the size of any fluid inclusions and, in aspects, without any use of fluid inclusion characteristics (such methods do not necessarily exclude the comparison or combination with fluid inclusion characteristic methods for determining carbonate rock characteristics, but, at least in part, do not rely on such characteristics).

According to aspects, the invention herein is a method of determining the carbonate grain size of a rock sample comprising (a) obtaining a rock sample from a geologic area expected or known to contain carbonate rocks; (b) subjecting the rock sample to conditions that cause the release of a detectable amount of carbon dioxide, one or more carbon dioxide-related compounds (CDRCs) (described herein), or a combination thereof from the rock sample, if present, (c) measuring the amount of carbon dioxide, CDRCs, or a combination thereof released from the rock sample, and (d) determining the carbonate grain size of the rock sample based upon the amount of carbon dioxide, CDRCs, or a combination thereof released from the rock sample. In aspects, an analysis of the relative amount(s) of carbon dioxide, CDRCs, or combinations thereof between samples are used to describe the relative carbonate grain sizes between samples, and/or, e.g., between geological regions or areas represented by the samples.

In aspects, the invention comprises applying methods described here to the analysis of at least 2, at least 5, at least 10, at least 50, or in aspects at least 100 rock samples sourced from regions of a geologic area that are at least about 10, at least about 25, at least about 50, at least about 75, at least about 100, at least about 250, or even more apart in at least one dimension from other regions of a geologic area. In aspects, performance of the methods of the invention can provide data from which a map of the carbonate grain size in a region can be developed. In aspects the geologic area is associated with petroleum exploration and/or petroleum production, and the rock sample(s) comprise petroleum drill cuttings. In aspects, data resulting from the invention described herein can be utilized to identify and select location(s) for drilling one or more petroleum wells or for directing the further exploration of a petroleum-related exploration or extraction operation, including the selection of a location of drilling, or extending a horizontal petroleum well and/or to select a location for fracking operations.

According to certain aspects, the inventive method is applied to identify regions in a geologic area associated with relatively low carbon dioxide or carbon dioxide-related compound released from rock samples known to include at least a substantial amount of carbonate rocks, such that a lack of such compounds is indicative of a high probability of the region containing a fault, or other method of subsurface pressure and $CO_2$ loss, as in communication with another well drilled nearby. In some aspects, the invention comprises directing petroleum production drilling operations based on the identification of an area that is likely to contain a fault by performance of the method.

According to yet further aspects, the inventive method is a method which can be used alone or in combination with other methods to identify the presence of, or the increased likelihood of the presence of, a fault comprising the analysis of two or more compounds having different mobility characteristics within a rock, wherein unexpected amounts or ratios of the two or more compounds within a sampled location which is different from surrounding sampled locations is indicative of such a location being associated with fluid transport, e.g., being associated with the presence of, or the increased likelihood of the presence of, a fault.

DETAILED DESCRIPTION OF THE INVENTION

Provided here are, in one embodiment, new methods for determining the average carbonate grain coarseness characteristic(s) of a carbonate rock sample. Typically, the carbonate grain content information obtained by performing the inventive methods described herein, e.g., by performing the $CDRC/CO_2$ methods described herein, comprises or consists of obtaining carbonate grain size information, such as the average carbonate grain size of a material comprising, consisting of, predominately comprising, or consisting essentially of carbonate rock material. As such, where terms such as "grain coarseness" are used herein such disclosure specifically implicitly simultaneously supports methods for determining carbon grain size information (e.g., the range of carbon grain sizes, the distribution of carbon grain sizes, and the like), specifically including determining the average carbon grain size of the material under analysis, and vice versa. Hence, provided here also are new methods for determining the carbonate grain size of a rock sample and for collections of rock samples from an area/site, formation, and the like.

In general, the inventive methods provided herein can include (e.g., $CDRC/CO_2$ methods) the steps of (a) obtaining a rock sample from a geologic area/site expected or known to contain carbonate rock; (b) subjecting the rock sample to conditions that cause the release of carbon dioxide, carbon dioxide-related compounds ("CDRCs"), or a combination thereof from the rock, if present in the rock, (c) measuring the amount of carbon dioxide, CDRCs, or a combination thereof released from the rock sample, and (d) determining the carbonate grain coarseness, e.g., the carbonate grain size, of the rock sample by measuring the amount of carbon dioxide, CDRCs, or a combination thereof released from the rock sample. The combination of these steps can be referred to as the "$CDRC/CO_2$ embodiments" of the invention, although numerous specific combinations and variations of such steps are provided herein, and the invention encompasses any suitable version of such $CDRC/CO_2$ methods comprising one or more of any such variations. Additional embodiments of the invention described below also do not rely on the assessment of $CO_2$/CDRC(s), do not entail determining carbonate coarseness/grain size, or do not comprise either thereof.

Typically, the analysis step of CDRC/$CO_2$ methods will include directly measuring carbon dioxide released from rock sample(s). In aspects, the primary analyte measured in such methods is carbon dioxide. In aspects, $CO_2$ is generally the only, substantially the only, or the only analyte measured in the determination of carbonate grain coarseness of sample(s). However, in other embodiments the invention includes also or alternatively analyzing the amount of one or more non-carbon dioxide "CDRCs." A CDRC (carbon dioxide-related compound) is a compound that (a) is chemically similar to carbon dioxide and found naturally within fluid inclusions and/or (b) is converted readily to carbon dioxide under the conditions that promote release of the compounds from the rock samples and/or capture of such volatile compounds for analysis. The most common CDRCs include carbonic acid ($H_2CO_3$) and bicarbonate ($HCO_3^-$). In another aspect, CDRCs also or alternatively include carboxylic organic acids such as formic and/or acetic acid. All of these compounds can produce gaseous $CO_2$ under gentle vacuum conditions (e.g., conditions comprising application of a pressure of about 1-about 100 millibars, applied for, e.g., about 0.15 to 15 minutes). In aspects, $CO_2$ and CDRCs can be interchanged, such that explicit disclosure of one of such compounds provides implicit support for the other type in any passage of this disclosure. However, at a more specific level such aspects can result in different analyses and involve different methods, which may lend to specific aspects directed to $CO_2$ or CDRCs (as a group, sub-group, or individually) being associated with properties that render such aspects substantially distinct from such other aspects.

Because carbonates are sedimentary rocks they can be characterized based on the size of particles ("grains") that make up the rock. As already noted, grain coarseness, inclusive of grain size, is an important characteristic of such rocks. For example, grain size can be correlated with the ability of an area of rock to hold or transmit fluids, such as petroleum products (e.g., oil, natural gas, and other fluids). It is my view that the size of fluid inclusions, cracks that contain volatile compounds (including micro-fissures and other "tight spaces"), and other, similar structural features in these rocks correlates with grain size. I have discovered that the quantity of compounds released from fluid inclusions, tight spaces in carbonate grain-rich material, and the like, including compounds dissolved in water or dissolved in oil or present in a gas, or any combination thereof, e.g., from a carbonate rock, can be used to rapidly and economically characterize the grain size of rocks, subject to consideration of possible loss of such fluid inclusion or other tight-space-compound-content, including those dissolved in water or oil or present as a gas. Such losses can occur due to the presence of a fault, or other pressure and fluid loss conduits (features that result in detectable or significant pressure loss), which is further discussed below (e.g., old boreholes)). The existence of tight spaces and similar structures in rock materials are identified by, e.g., the ability to extract volatile materials by application of relatively modest extraction forces, such as through the application of gentle vacuum extraction, described in my earlier published patent applications and issued patents (e.g., the RVS applications, cited elsewhere).

CDRC/$CO_2$ methods can be applied to any suitable material, such as a material that (a) comprises a detectable amount of, (b) comprises in substantial part (e.g., making up at least about 10%, at least about 20%, at least about 25%, or at least about 33% of a material), (c) predominately comprises, (d) is substantially composed of (e.g., at least about $\tfrac{2}{3}^{rd}$ of the material being composed of, at least about 75% of the material being composed of, or at least about 90% of the material being composed of), (e) consists nearly entirely of (at least about 95%, at least about 99%, or more is made up of), (f) consists essentially of, or (g) consists of (at least within limits of detection) carbonate rock materials.

Although the operability of the inventive method is not restricted by theory, I believe that a thermodynamic equilibrium exists for carbon dioxide between carbonate minerals and their associated, e.g., counterpart/equilibrated waters, which may make it possible for analyze carbonate grain content using the methods described above. Carbonates typically have carbon dioxide as part of their crystalline structure, hence a carbonate mineral in equilibrium with associated water will buffer that water to provide an equilibrated amount of carbon dioxide in solution as dissolved carbon dioxide, bicarbonate, and carbonic acids. Factors such as salinity, ionic composition of the material(s) and water, pH, pressure, and temperature can impact this buffering effect, but may be within limits that would likely be encountered in many situations. Carbon dioxide in such associated aqueous solutions (e.g., the aqueous phase of a mixed sample) may be buffered and the method can be characterized in being performed using such material or applying the general method or a variant thereof to a material obtained from an environment having such characteristics. Clastic rocks/sediments typically do not have carbon dioxide in their structure and, as such, the carbon dioxide content of clastic sediment-associated water varies significantly as compared to the restricted range of carbon dioxide found in water associated with most carbonates. The practice of the method on material associated with the type of buffered water solutions normally associated with carbonate materials is an aspect of the inventive method.

Carbonate grain sizes have been well characterized based on focused rock studies. In general, grain sizes having a diameter of 0.25 mm or smaller will typically be considered "fine", whereas grain sizes having a diameter of 0.5 mm or larger will be considered "coarse", with the range of 0.25-0.5 mm diameter being considered "medium." The following Wentworth grain-size scale for sediments, showing Wentworth size classes, equivalent phi ($\phi$) units, and sieve numbers of U.S. Standard Sieves corresponding to various millimeter and $\phi$ sizes, in chart form obtained from Boggs, "Principles of Sedimentology and Stratigraphy", Fourth Edition, Pearson Education, Inc., Upper Saddle River, NJ, ©2006, 2001, 1995, (FIG. 7) is provided to aid in the characterization of coarse and fine grains.

In aspects, CDRC/$CO_2$ methods are applied to samples of rocks collected from one or more locations of a geologic area, such as a petroleum exploration or production site. This can be also true of other methods of the invention, such as the compound size quantity differentiation ("CSQD") methods described below. In either case, the analyzed samples can be in any suitable amount and collected in any suitable style. In some cases, the samples are collected and washed prior to storage or analysis. In other cases, samples can be sealed at the site of collection, e.g., soon after extraction from the well or other target geologic area (e.g., within less than about one week, less than about 48 hours, less than about 24 hours, less than about 18 hours, less than about 12 hours, less than about 10 hours, less than about 8 hours, less than about 4 hours, less than about 2 hours, or less than about 1 hour). In some cases, the samples are collected in a container that is impervious to the release of volatile compounds, such as are described in detail within the RVS applications. Alternative to applying the method on samples, it may be possible to apply the methods of the invention to rocks in situ (i.e., in the geologic formation). In most cases, however, it will be practical to apply the method to samples of rocks obtained from the geologic area and to relate the results obtained by applying the method to the sample to characterize the general nature of the area represented by the samples.

The geologic area that is subject to testing or from which materials are collected will typically be known to include some amount of carbonate rocks or will be expected to contain such rocks based on knowledge from the surrounding area, other geological analysis, or the like. In some cases, the geologic area will be known to be associated with such rocks through observation (e.g., by geologic survey) or by some previously applied analysis of rock contents prior to performing the method. For example, in certain areas of Oklahoma and the Middle East extensively drilled for oil production and exploration, it is well known that the entire area is composed of, at least in substantial part, carbonate rocks. In other aspects, the method can be applied to geographic regions/geographic areas or sample collections from such regions/areas not known to include carbonates or where the carbonate content has not been identified or predicted, and the results of the method are used to assess the nature of any newly discovered carbonate rocks' coarseness, assuming that the geological results are indicative of carbonate rocks being present in the samples/area. In aspects, rock sample(s) can be subjected to select conditions causing the release of carbon dioxide, CDRCs, or a combination thereof from the rock, which can be used to determine, e.g., related to, correlated to, or otherwise indicative of, the carbonate grain coarseness, specifically the carbonate grain size, of the rock sample, and hence the carbonate grain size of the rock within the region/area represented by the sample. In aspects, a determination of relatively higher coarseness in an area or part of an area provides a basis for the prediction of relatively higher quantities of petroleum product(s) in the area. In aspects, such data is combined with one or more other relevant analytical data sets, such as data obtained by performing other aspects of RSV methods described in the RSV applications on the samples or related samples, or data obtained by applying other relevant methods for characterizing the likelihood of petroleum productivity associated with an area, such as those described elsewhere herein or that are otherwise known in the art.

The rock sample or rock samples are typically subjected to conditions that cause the release of carbon dioxide, CDRCs, or a combination thereof ("$CO_2$-volatiles"; the term $CO_2$-volatiles inclusive of $CO_2$ alone, one or more CDRC (s), or a combination of any or all thereof). The conditions can be passive conditions, but typically will include the application of one or more forces to the samples. In one embodiment, the release of volatiles that can comprise $CO_2$-volatiles includes release of gas and/or liquid from fluid inclusions and/or cracks (such cracks can be referred to as tight spaces, e.g., spaces within or between carbonate grains) contained in the rock samples. In one aspect, the conditions that cause release of the carbon dioxide, CDRCs, or combination thereof include physically disrupting the rock sample, such as through crushing the samples. In one aspect, the crushing is performed on samples that are in a crushable and selectively traversable container, such as the selectively puncturable containers described in the RVS applications. "Traversable" in this respect means that the container can be selectively punctured, entered, or otherwise accessed by a needle or similar flow path device allowing for gasses contained therein to be withdrawn for analysis. The conditions that cause release of $CO_2$-volatiles also or alternatively can include application of pressure, or application of the various other methods described in the RVS applications and as also discussed and exemplified further herein. The assessment of the carbonate grain size of the rock sample, and, thus, the geologic area provided sufficient samples are analyzed in the performance of the method (e.g., at least about 10, at least about 20, at least about 25, at least about 40, at least about 50, at least about 100 or more samples are analyzed), can be a relative assessment (e.g., identifying areas of relatively high and relatively low grain sizes by relatively high and low amounts of $CO_2$ and/or CRDC release, as exemplified in the Examples section contained herein). The use of multiple samples also can be a component of CSQD methods. In another aspect, CDRC/$CO_2$ methods can be applied against a previously developed scale and/or other objective information that can provide a more quantitative analysis of the grain size content through the correlation with $CO_2$ and/or CDRC release. This is discussed further elsewhere herein.

In many facets of the invention, the inventive methods (e.g., CDRC/$CO_2$ methods, LVCFI methods, and CSQD methods) are performed on several samples from one or more site(s), such as at least about 10, at least about 25, at least about 50, at least about 75, at least about 100, or more, such as at least about 200, 250, 300, 350, 500, 750, about 1000, or even more samples, which are typically spaced apart from each other in different regions of the geologic area of interest. Thus, for example, such sample in a collection of samples in methods of the invention may be separated by a distance of at least about 20, at least about 50, at least about 75, at least about 100, at least about 200, at least about 300, at least about 500, at least about 600, or at least about 1000 feet from each other in at least one direction. In aspects, most, generally all, substantially all, or all samples analyzed in a method are spaced apart from one another by a distance in at least one direction characterized by falling within a range based on any combination of such recited distance values (e.g., about 50-about 1000 feet, such as about 100 feet to about 600 feet, or about 200-500 feet, etc.). Such distances can be readily obtained by, e.g., collection of cuttings obtained from different regions of a well (either vertically or horizontally) or exploration area, which can be collected by periodically sampling cuttings as they are produced at the site of drilling.

Typically, the $CO_2$ or CDRC ($CO_2$ volatiles) content of analyzed samples collected from a single geological location, e.g., a single geological formation, (e.g., from a single well), representative of varying physical locations within the formation or well, can be combined to create a single visual representation of $CO_2$ or CDRC content across a formation. That is, in aspects, the $CO_2$ or CDRC ($CO_2$ volatiles) content of analyzed samples collected from a single geological location, e.g., a single geological formation, (e.g., from a single well) is representative of carbonate grain size of the rock in the locations from which each sample was obtained, and such identified grain size(s) for each sample can be combined to create a single visual representation of the grain size of the carbonate rock across the location, formation, or, e.g., well, of which the samples are representative. This approach is exemplified in the included Figures and Examples. The $CO_2$ or CDRC level as measured from samples of a specific location within a formation can be, e.g., in aspects, plotted on a single graph by both units of $CO_2$ or CDRC (e.g., as measured by mass spectrophotometric response i.e., in a digitized voltage reading) and physical location (e.g., depth of a well). $CO_2$ or CDRC content can in aspects then be used to assess the carbonate grain size, as $CO_2$ or CDRC content is correlated with grain size of the sample on which the analysis is being conducted. In aspects, a higher $CO_2$ or CDRC level, e.g., a higher $CO_2$ volatiles level, will then typically be representative of rock with a larger (typically larger mean/median) carbonate grain size; e.g., grain size of 0.25 mm or higher, for example about 0.30 mm, about 0.35 mm, about 0.50 mm, about 0.75 mm, about 1 mm, or even greater). A lower $CO_2$ or CDRC level, e.g., a lower $CO_2$ volatiles level, will correspondingly typically be interpreted as representative of rock with a smaller (typically small average/median) grain size; e.g., grain size of about 0.25 mm or smaller, for example about 0.20 mm, about 0.1 mm, 0.09 mm, 0.08 mm, 0.07 mm or even smaller, for example 0.06 mm or less).

The grain size of rock, can, in aspects, be correlated with the size of fluid inclusions, volatile-containing cracks or volatile-containing tight spaces within or between carbonate grain(s), other structures/elements of the carbonate rock that contain volatile compounds, such as $CO_2$ and/or CDRCs (the $CO_2$ and/or CDRCs ($CO_2$ volatiles) therein being present as a gas, dissolved in water, dissolved in oil, or any combination thereof). That is, in aspects, the larger the grain size, it is typically expected the larger the fluid inclusion(s), cracks, and/or other structures described above, and which are otherwise similar in nature and present within the rock. Correspondingly, the smaller the grain size, the smaller the fluid inclusion(s) and/or cracks or such other structures. Rock(s) comprising a large grain size can contain small volume fluid inclusions in addition to small diameter cracks and voids. However, such small features have a high likelihood (e.g., in 90% or more cases) of being volumetrically insignificant relative to the larger fluid inclusions, cracks, and voids in the large grain size rock. As an example, a spherical fluid inclusion having a diameter of 10 microns has a volume which is 1000 times higher than the volume of a spherical fluid inclusion having diameter of 1 micron. It therefore may be established, that the higher the level of $CO_2$ or CDRC, e.g., $CO_2$ volatiles, in sample(s) as measured by the method(s) described herein, the higher the grain size of the rock from which the analyzed sample was taken, and the higher the grain size, the larger fluid inclusion(s), cracks, and other structures containing $CO_2$-volatiles are likely present in rock from which the sample(s) was/were taken. Making such determinations is yet another aspect of the invention.

In aspects, such $CO_2$-content data can be used to identify patterns, maps, and/or other positional characteristics of rock samples, e.g., of carbonate rock(s), from the same borehole. In alternative aspects, such $CO_2$-content data can be used to identify patterns and/or other characteristics of the samples of carbonate rock(s) from boreholes drilled using the same or comparable drilling techniques.

In aspects, within an individual borehole, and within a collection of two or more similarly drilled boreholes (e.g., boreholes drilled utilizing the same or comparable drilling technology), mechanical disruption of similar rocks is fairly consistent (e.g., not significantly differing as compared to distinct rocks, rocks from different locations, or both). E.g., in aspects, within a borehole or across boreholes drilled using comparable drilling technology, the mechanical disruption is such that the mechanical disruption from the resulting samples varies by no more than about 20%, no more than about 15%, no more than about 10%, no more than about 5%, or by no more than about 1% from sample to sample.

In aspects, the average size of the rock material in a sample varies by no more than about 20%, no more than about 15%, no more than about 10%, no more than about 5%, or by no more than about 1% from sample to sample, in most, generally all, or all samples, or on average. However, alternatively, such relative consistence can be lost across boreholes if such boreholes are drilled using different drilling technologies or drilling practices. For example, in aspects, a higher amount of $CO_2$ would be expected to evolve from the rock sampled from a borehole drilled using a rock bit, which provides relatively large cuttings pieces, than would be expected to evolve from the same rock if the borehole were drilled using a PDC bit, which provides relatively small cuttings pieces. Further, an even higher amount of $CO_2$ can be expected to evolve from the same carbonate rock if the borehole were to be cored. In aspects, scaling factors can be applied to reconcile such differences in released $CO_2$ caused by differences in drilling technologies or drilling practices. In aspects, such scaling factors can be calculated by comparing results of analysis from similar rocks obtained from wells drilled using differing technologies or practices. Once established, such scaling factors could then be used to reconcile data collected from such varied wells. In aspects, the application of such scaling techniques described here can allow for a regional mapping of the results from a variety of wells even if wells of the region were drilled utilizing differing techniques or practices. The development and application of such scaling factors through the practice of the methods described herein is yet another aspect of the invention.

Measurements of CDRC/$CO_2$-volatiles from rock samples can be made in a relative fashion, as the exact composition of each sample may or may not be known. Therefore, the described method may describe the rock as characterized by the present analysis as a "type"; for example, as Type I or Type II rock, as exemplified in the Examples and Figures provided herein. While for exemplary purposes the terms "Type I" and "Type II" have been used, it should any other characterization may be utilized in which a distinction is drawn between rock having differing $CO_2$ and/or CDRC characteristics as determined by the present method. Further more than two such "types" can be described, such as about 3, about 4, or about 5 or more such classifications of "type" can be provided, depending on the level of refinement suitable and/or otherwise desired for a particular analysis. Exemplary images of two types of rock distinguishable by the methods herein, e.g., a "Type I" and a "Type II" rock are provided as FIGS. 2A and 2B. FIG. 2A illustrates a first type of rock, characterized as "Type I" in the present invention (a bioherm carbonate), with the largest grain size, largest fluid inclusions, and corresponding highest $CO_2$ release of the two rock types studied in the Examples. FIG. 2B illustrates a second type of rock, characterized as "Type II" in the present invention (crinoidal grainstone), where grain size is large but smaller than that of Type I, with large fluid inclusions, though smaller than that of Type I, and with a distinguishably lower $CO_2$ release than that of Type I.

In certain other embodiments, the $CO_2$ and/or CDRC content of a sample or samples as determined by the present method can also or alternatively be compared against one or more established scale(s), wherein the $CO_2$ and/or CDRC result, when read from one or more established scales, allow one to identify additional characteristics of the rock from which the sample or samples came, including but not limited to specific rock type, specific grain size, specific grain pattern or "fabric" of the rock, specific fluid inclusion/crack size or level of presence, for example percent of rock composition, or other characteristics of the source rock such as specific mineral content or compositional elements.

In another aspect, the invention provides a method of generating such one or more scale(s) by application of the method to a set of rocks having discrete properties under certain conditions and plotting out the release of $CO_2$-volatiles therefrom, often in a process that is repeated several times so that the data obtained from such multiple analyses can be combined through averaging or statistical methods to provide a reliable scale.

In one aspect, the invention provides methods of developing a scale for determining the carbonate rock type, specific grain size, specific grain pattern or "fabric" of a rock, specific fluid inclusion/crack size or level of presence of a rock sample based on the amount of $CO_2$-volatiles released therefrom, comprising (a) performing the herein described methods of analyzing $CO_2$-volatiles and identifying the carbonate rock type, specific grain size, specific grain pattern or "fabric" of the rock, specific fluid inclusion/crack size or level of presence in a plurality of samples; (b) combining the data accumulated on the plurality of samples into one or more scale-defining data set(s); (c) optionally further processing the data of each scale-defining data set to obtain scale(s) against which either 1) knowing the $CO_2$-volatiles of an analyzed sample allows one to utilize the scale to obtain a predicted carbonate rock type or average carbonate rock type, average grain size, average or characteristic grain pattern or "fabric" of the carbonate rock, average fluid inclusion/crack size or expected level of presence of the sample; 2) knowing one or more of the characteristics of (1) of an analyzed sample allows one to utilize the scale(s) to obtain a predicted average $CO_2$-volatiles released from such a sample upon application of the method(s) described herein; or 3) both (1) and (2) are true. In aspects knowing the $CO_2$-volatiles of an analyzed sample allows one to utilize a single scale to obtain a single predicted value or single predicted characteristic, such as, e.g., one of a predicted rock type or average carbonate rock type, average carbonate grain size, average or characteristic grain pattern or "fabric" of the carbonate rock, average fluid inclusion/crack size or expected level of presence of the sample. In alternative aspects, knowing the $CO_2$-volatiles of an analyzed sample allows one to utilize a single scale to obtain multiple predicted values or multiple predicted characteristics, such as, e.g., two or more of a predicted rock type or average rock type, average grain size, average or characteristic grain pattern or "fabric" of the rock, average fluid inclusion/crack size or expected level of presence of the sample. In aspects, such scales are specific to individual boreholes or to boreholes drilled using the same or comparable drilling techniques, technologies, or practices.

In certain aspects, an exemplary method of developing a scale described above, such as but not limited to a CDRC/$CO_2$-volatiles-carbonate grain size scale, can comprise the use of at least about 2, at least about 5, at least about 10, at least about 50, or in aspects at least about 100 rock samples, such as at least about 250 rock samples, at least about 500 rock samples, at least about 750 rock samples, at least about 1000 rock samples, at least about 1250 rock samples, at least about 1500 rock samples, at least about 1750 rock samples, at least about 2000 rock samples or even more, such as at least about 3,000, 4,000, 5,000, 6,000, 7,000, 8,000, 9,000, or 10,000 or more rock samples from an individual borehole or from a plurality of boreholes drilled using the same or comparable drilling technologies, techniques, or practices.

In aspects, a method of developing a scale described above, such as but not limited to a $CO_2$-volatiles-carbonate grain size scale described above, can comprise use of a plurality of rock samples which are representative of the broadest range of reasonably expected possible carbonate grain sizes, reasonably expected possible $CO_2$-volatiles, or both, to be encountered in samples with which the scale is used as a part of a sample analysis from an individual borehole or from a plurality of boreholes drilled using the same or comparable drilling technologies, techniques, or practices. In aspects such a characteristic as carbonate grain size can be replaced by, e.g., one or more other characteristics such as but not limited to average fluid inclusion size; however, carbonate grain size is utilized here for purposes of simplifying the description. In aspects, a sufficient number of samples having the lowest reasonably expected possible carbonate grain size, a sufficient number of samples having the highest reasonably expected carbonate grain size, a sufficient number of samples having the lowest reasonably expected $CO_2$-volatiles, a sufficient number of samples having the highest reasonably expected $CO_2$-volatiles, and a sufficient number of samples within each such range, are utilized in the production of the scale, such that use of the scale from an individual borehole or from a plurality of boreholes drilled using the same or comparable drilling technologies, techniques, or practices provides data that is suitably reliable; e.g., (a) the data provided by the scale is accurate to within at least about 50%, at least about 60%, at least about 70%, at least about 80%, at least about 90%, at least about 95%, or more of the actual carbonate grain size if reading the carbonate grain size from the scale, when an amount of $CO_2$-volatiles is known, at least about 50%, at least about 60%, at least about 70%, at least about 80%, at least about 90% or more of the time; (b) the data provided by the scale is within at least about 50%, at least about 60%, at least about 70%, at least about 80%, at least about 90%, at least about 95%, or more of the actual CDRC/$CO_2$-volatiles value if reading the CDRC/$CO_2$-volatiles from the scale, when the average carbonate grain size is known, at least about 50%, at least about 60%, at least about 70%, at least about 80%, at least about 90% or more of the time; or (c) both (a) and (b) are true.

In certain embodiments, the inventive methods provided here (e.g., CDRC/$CO_2$ methods, LVCFI methods, and CSQD methods) can be applied to samples obtained from a geological area/site, formation, or formations known to contain carbonates, e.g., predominantly carbonates, such as by applying the method in the carbonate-rich areas of Oklahoma, United States of America, where a significant amount of oil production and exploration is underway at the time of this application. In alternative embodiments, the method may be applied to samples collected from geological formations where carbonate composition may be unknown or less characterized.

In certain embodiments, inventive methods (e.g., CDRC/$CO_2$ methods, LVCFI methods, and CSQD methods) described herein are performed on multiple rock samples, e.g., a plurality of rock samples, such as, for example, about 2, 5, 10 or for example about 25, 50 or more samples, for example about 100, 250 or about 500 or more samples or up to about 750 to about 1000 samples or more. In aspects, samples can be obtained from at least two regions of a geologic area, for example about 2, 3, 4, 5, 8, or about 10 different physical locations of a geologic area, for example at least about 15, 20, about 50 or more regions of a formation, e.g. about 60, 75, 100, 125, or up to about 150 or about 200 or more locations within a geologic area, the physical distance between such samples being greater than about 6 inches, for example about 1, 2, 3, about 5 or about 10 feet, and often greater than about 15, 25 or about 50 feet, e.g. about 60, 70, 80, about 90, or about 100 feet or more, such as about 120, 140, 160, 180, or about 200 or more feet in a single direction. The distance between samples analyzed from the same geologic formation in some embodiments may be in a horizontal direction. In alternative embodiments, the distance between samples analyzed from the same geologic formation may be in a vertical direction. In some cases, samples that are distinguished in both horizontal and vertical directions are provided, or two sets of samples, one differing in terms of vertical placement in the area/well and the other different in terms of horizontal placement in the area/well are obtained/provided and subjected to analysis through the inventive method. Skilled persons will note that although aspects of this disclosure include lists of suitable numbers of values, as recited above, there can be significant differences in methods characterized by such different values. Skilled persons will understand that in cases any of such values, or at least sub-sets of such values (e.g., values around either end or the middle of a range of values), can have significantly different properties from each other and, accordingly, can at a more precise "level" of analysis, differ significantly from each other and represent independent aspects of the invention from one another.

Multiple terms are used here to describe geological areas which can be analyzed using the methods of the invention. In aspects, the terms "area" or "region" can be used generally and should be interpreted to mean a zone or locality, which can be a single feature (e.g., a single "site" such as a well) or can be, for example, an expanse comprising multiple features (e.g., an expanse comprising multiple wells). The terms "area" or "region" is often referred to in the art as a division of a play (described below). As used herein, the terms "area" or "region" can refer to any zone or locality sampled and under analysis.

A "formation" is understood in the art to mean an identified area of strata having similar lithology. In some cases, a formation also may be defined by other characteristics, such as biostratigraphic characteristics, chemostratigraphic characteristics, or both, and sometimes such characterizations of a formation are used interchangeably. Typically, a formation is a series of strata/beds that is distinct from other beds above and below and is thick enough to be shown on the geological maps that are widely used within the area in question. Formations dominated by a rock typically include the dominant rock in the formation's name (e.g., the "Woodford Shale Formation" found in several parts of Oklahoma). However, formations in some cases can contain a variety of related or interlayered rock types, such as the Summerville Formation of Utah, which consists of thin alternating beds of shale, siltstone, and sandstone. Formations can be divided into sub-formations or "members" based on such characteristics.

In petroleum production the term "play" is used to indicate a region defined by a group of oil fields (each comprising many wells/sites) that generally share the same set of geological circumstances (e.g., formations present). Oklahoma, USA, for example, has many plays but two notable ones making headlines across the nation are the "SCOOP" (South Central Oklahoma Oil Province) and the "STACK" (Sooner Trend Anadarko Basin Canadian and Kingfisher Counties). The petroleum-rich STACK play is characterized by presence of Oswego, Meramec, Osage, and Woodford formations. Plays can be divided into "regions" or "areas" comprising two or more (often several) sites, potential sites, or both. A typical "site" is a petroleum well or an area of prospective petroleum drilling within an area or play. In aspects, related samples can be obtained from multiple sites within a single play.

In some embodiments, methods of the invention are performed on at least 2 rock samples, for example about 2, 3, 5, 7, about 9, or about 10 samples, for example about 20, 50, 75, or about 100 samples, or more, e.g. about 150, 200, 300, 400, 500, 600, 700, 800, about 900, or for example about 1000 or more samples, wherein such samples are sourced from regions of a single geologic area that are separated by some physical distance, for example about 6 inches, for example about 1, 2, 3, about 5 or about 10 feet, for example about 15, 25 or about 50 feet, e.g. about 60, 70, 80, 90, or about 100 feet or more, such as about 120, 140, 160, 180, about 200 or more feet in a single dimension and physically distinct from all other regions.

In aspects, CDRC/$CO_2$ methods comprise analyzing the predicted coarseness resulting from the $CO_2$ or CDRC data for such samples and mapping the coarseness-results by physical location of the samples on which the analysis was performed, to provide a map of the carbonate grain size of materials within areas of the geologic site/area analyzed. In certain embodiments, the method comprises generating a physical map of the region. In alternative embodiments, the map that is generated also or alternatively is a digital map or plot of the region reflecting the carbonate grain size of the carbonate rock-containing structures in the region, and optionally the presence of suspected faults based on other aspects of the inventive method described further herein. Thus, in certain embodiments, a map can contain specific $CO_2$ or CDRC ($CO_2$ volatiles) content results by region. In embodiments, such a map can contain correlating carbonate rock grain size, correlating rock fluid inclusion size or presence level, gamma ray analysis results or other geological or non-geological characteristics of the region. Such results can, in aspects, be obtained through alternative aspects of the method described herein or be obtained through separate data collection or analysis.

In certain embodiments of the current invention, the step of subjecting the rock samples to conditions that allow for, promote, induce, or cause the release of volatile compounds, including $CO_2$-volatiles, if present, comprises a physical disruption of the rock sample being analyzed such that any amount or any significant amount of volatiles contained within the rock sample are released. In aspects, while physical disruption of the rock sample being analyzed can release any amount or any significant amount of volatiles contained within the rock sample, no significant amount of structural $CO_2$ is released which significantly impacts the $CO_2$ analysis; that is, in aspects, at least about 80%, at least about 85%, at least about 90%, at least about 95%, at least about 97%, at least about 99%, or even more is $CO_2$ present within the rock but not a component of the crystalline structure of the rock. In certain embodiments, such a disruption is a squeezing, smashing, exploding, and/or a crushing of the samples. In alternative embodiments, the physical disruption can be accomplished through sawing, tumbling, or exposing the sample to vibrational energy at any number of frequencies. In yet further alternative embodiments, the integrity of the sample can also or alternatively be disrupted through the application of heat; one effect of which can be disruption of the sample by thermal decrepitation of fluid inclusions and/or other structures in the sample. In aspects, however, the application of heat in most, generally all, or all steps of the method is limited to time and temperatures low enough not to cause detectable or significant release of structural $CO_2$ contained in the mineralogical structure of the carbonate grain (e.g., less than 5%, less than 2%, less than 1%, less than 0.5%, less than 0.1%, less than 0.05%, or less than 0.01% of the $CO_2$ analyzed in a method is from release of structural $CO_2$ in samples or analyzed material). In further embodiments, disruption also or alternatively can be accomplished through the application of chemical processes and/or application of energy also or alternatively may be applied to the sample in the performance of the method, such as, for example, applying an acid to the sample so as to dissolve certain substances. Again, however, in aspects use of acid(s) does not cause detectable or significant release of $CO_2$ from the mineralogical structure of samples. Also or alternatively, the use of pressure, for example vacuum pressure, can be used to disrupt the sample causing any volatile substances held within the sample to be released. It is also possible that in some instances a combination of two or more of these or other physically disruptive processes may be usefully applied in the practice of the inventive methods (e.g., $CDRC/CO_2$ methods, LVCFI methods, and CSQD methods). The combination of physical disruption, e.g., squeezing, and application of a gentle vacuum, as discussed in the RVS applications, is a particularly advantageous method for promoting the release of $CO_2$-volatiles from rock samples.

In certain aspects, the invention can be characterized as analyzing $CO_2$, CDRCs, or both ($CO_2$-volatiles) in samples wherein the samples are not chemically decomposed as a part of the method. In aspects, $CO_2$ maintained as a part of the mineral's crystalline structure is not released and does not provide a detectable or significant amount of $CO_2$-volatiles measured in the method(s) described herein. In certain aspects, the methods described herein do not cause break down of carbonate minerals. In certain aspects, a breakdown of carbonate minerals would overwhelm, or "swamp" the much smaller amount of $CO_2$, CDRCs, or both ($CO_2$-volatiles) measured in the methods of the present invention, rendering the method unworkable. In aspects, the method(s) described herein are unrelated to how much of a rock is made of carbonate mineral(s) but is instead related to describing the size of the carbonate grain within analyzed rock.

In certain embodiments, the inventive method is applied to samples collected from a geologic area associated with petroleum exploration and/or production. In certain embodiments, the inventive method is used alone or in combination with one or more other methods to assess the feasibility of successful petroleum exploration or production within a geologic area. Also or alternatively, the method can be used in areas where there is no active petroleum exploration or production. In alternative embodiments, the method can be applied to samples collected from areas where the feasibility of petroleum exploration or production is completely unknown.

In certain embodiments, samples used in the described invention are cuttings from a drilled petroleum well. Cuttings are well known in the art and described in the RVS applications and other incorporated patent documents. In alternative embodiments, samples used in the described invention can be other types of samples not associated with oil drilling operations. In certain embodiments, the cuttings are sealed at the well cuttings. In alternative embodiments, the cuttings are not sealed at the well. In yet further alternative embodiments, samples can consist of or comprise drilling mud. In some respects, the samples are or comprise cuttings that were obtained from wells drilled with oil-based muds (OBMs) and in other aspects the samples are or comprise cuttings that were obtained from drills produced from water-based muds (WBMs).

In aspects, at least about 10%, at least about 20%, at least about 25%, at least about 33%, at least 50%, or more of the samples are cuttings produced by Polycrystalline Diamond Compact (PDC) bit drills. PDC bit drills produce significantly smaller cuttings than previously used drilling methods (e.g., producing significantly smaller cuttings than other drilling methods known and utilized in the art). Because these drills can be more effective in certain conditions, they are increasingly in use. The ability of the inventive method to be successfully applied to such cuttings can be one important advantageous property of the method.

The results of applying the inventive method can be advantageously combined with one or more other geological analytical methods to better characterize the geologic nature of the area. For example, the results of the inventive method can be co-analyzed with the results obtained by gamma ray analysis of the area and/or rock samples. In this or any other method in which analytical methods are combined with the analytical methods of the present invention, the methods may either be applied to the same rock samples or to rock samples that are either known or expected to correspond to each other in terms of the region of the geologic area from which the samples originated. As noted, gamma ray methods are known in the art. The novelty of their use in this respect is in the combination of the results of such methods with the results of applying the present inventive methods to rocks, especially to rocks that may include carbonate rocks. The combined results of such methods can confirm each other and/or provide a more complete picture of the geologic nature of the area in question.

Other methods that also or alternatively can be similarly combined with methods of the invention include conventional well (resistivity) logging and/or fluid inclusion analysis, e.g., as described in my prior patents/applications. Results of $CDRC/CO_2$ methods can also or alternatively be combined with data from rock volatiles stratigraphy (RVS), focused on other volatiles, such as $C_4$-$C_{14}$ hydrocarbons, water, or other compounds, as described in the RVS applications.

Although RVS-related methods (such as application of gentle vacuum conditions) are one useful way, and often can be a preferred way, to perform steps (b) (subjecting the rock sample to conditions that cause the release of carbon dioxide, carbon dioxide-related compounds (CDRCs), or a combination thereof from the rock, if present in the rock) and (c) (measuring the amount of carbon dioxide, CDRCs, or a combination thereof released from the rock sample) of $CDRC/CO_2$ methods, other methods known in the art also or alternatively can be used to perform these steps. For example, such methods can include but may not be limited to methods involving relatively high-pressure vacuum conditions and/or other extraction techniques (e.g., exposure to high heating, as long as, as has been previously described, such heating does not cause the release of $CO_2$ held within the mineralogical structure of the carbonate grains). In aspects, no step for extraction of $CDRC/CO_2$ volatiles or any other volatiles obtained in a method of the invention results in the destruction/loss of more than about 10%, more than about 25%, more than about 50%, more than about 75%, more than about 90%, or more than about 95% of volatiles associated with tight spaces, micro-fissures, and the like (or any other volatiles that would be obtained by, e.g., application of gentle vacuum methods under sealed conditions).

In aspects, method of the invention can further include performing fluid inclusion analysis methods on samples, materials, or related samples/materials (such as the methods described in, e.g., U.S. Pat. Nos. 6,661,000 and 5,328,849, which describe earlier inventions by me and my co-inventor colleagues, as well as, e.g., methods described in, e.g., U.S. Pat. Nos. 7,395,691; 7,794,527; and 7,210,342 by Fluid Inclusion Technologies, Inc., now part of Schlumberger, which are, at least in part, also related to or built upon my earlier inventions and/or other work I was involved in). For example, in one aspect, methods comprise analysis of sample/material associated fluids, wherein at least about 33%, at least about 50%, at least about 66%, at least about 75%, at least about 90%, or at least about 95% (e.g., about 99% or more) of the fluid analyzed in the performance of the method is obtained from sample/material fluid inclusions, typically with the remaining fluid being associated with rock volatiles. In one aspect, the fluid in the material or the fluid analyzed in the performance of the method consists of or consists essentially of fluid released from fluid inclusions in the sample/material. In other aspects, the methods are performed primarily on fluids not obtained from fluid inclusions. In aspects, methods do not include inclusion of fluid inclusions. In aspects, fluid from fluid inclusions makes up less than about 20%, less than about 10%, less than about 5%, or less than about 1% of the fluid analyzed in the method.

The methods of the invention can, in aspects, be useful for a number of applications. In one aspect, the results obtained by analyzing an area (e.g., a petroleum well, a geologic formation, or a geologic region/area) through application of the method are used in guiding petroleum production planning and operations. For example, the results of the method can be used to select a location ("landing") for the placement of a horizontal well. In another aspect, the results of the method can be used to select among potential sites for fracking operations or to assess whether fracking is expected to be economically rewarding above or below a pre-set target that factors in the production that can be obtained from the rock of the geologic area to be fracked. In aspects, results of the method can aid in the determination of site(s) for the drilling of new petroleum wells having a high probability of producing petroleum, and/or the method can aid in the determination of which sites of a plurality of sites have a higher likelihood of productivity or a likelihood of having a higher level of productivity. In aspects, such advantages are especially useful in areas of petroleum exploration or production comprising carbonate rock(s).

Another aspect of the invention provides a method of identifying regions in a geologic area that are more likely than other regions to contain a fault. In aspects, such a method can be useful in that faults can provide areas for rapid production of petroleum given the ability of fluids to travel through the fault. The method also can be important in other ways, such as identifying areas that are unsafe for certain types of activities given the presence of an identified fault.

An exemplary embodiment of the invention comprises method(s) including (a) subjecting rock samples obtained from a plurality of separated sites in the area to one or more conditions that can cause the release of $CO_2$ and/or CDRCs ($CO_2$ volatiles) from the samples, if present, (b) measuring the amount of $CO_2$ and/or CDRCs that are released from the rock samples, and (c) identifying regions in the area that are associated with a relatively low amount of $CO_2$ and/or CDRC release compared to other regions in the area, wherein the regions identified as having a relatively low amount of $CO_2$ or CDRC release compared to others are likely to contain a fault. Such results, which indicate or at least suggest the loss of $CO_2$ from an area of rock that is expected to contain an amount of $CO_2$ (e.g., a carbonate having medium or large grains) likely reflects that a fault is in the area, which has permitted such volatile compounds to escape the region. This concept is exemplified in some of the Examples and Figures provided herein. This aspect of the invention, however, need not be limited to carbon dioxide and CDRCs, but can, in aspects, also be applied to other compound(s) that can be identified through rock volatiles stratigraphy, using the methods provided in the RVS applications, as similar losses of other volatile compounds may occur with the presence of a fault. Accordingly, such methods of the invention can be referred to as low volatile content fault identification (LVCFI) methods. In some embodiments, this type of inventive method is combined with other techniques for identifying faults that are known in the art, such as seismic refraction, seismic reflection, and resistivity methods. These methods also can be combined with the other methods of the invention, such that a geologic area can be characterized, in part, based on the carbonate grain size, and, in part, based on the presence of expected faults in carbonate-containing regions. The application of RVS methods to identify faults in such a manner need not be limited to carbonate materials or materials comprising carbonate materials but can be applied to any rock that is amenable to RVS analysis. An example of the application of RVS methods and analysis to so identify faults in non-carbonate materials is provided in Example 4 and FIG. 6.

In still another embodiment, the invention herein provides a method of identifying a fault, or the likelihood of the presence of a fault, within an area evaluated by analysis of samples collected therefrom, or a similar condition in or associated with a site (such as another conduit, a migration of fluids in part of the site, or both) comprising the comparison of two or more compounds/indicators having a difference in size, weight, or mobility. Such methods can be characterized as CSQD methods. In aspects, such an analysis comprises the comparison of a ratio of two or more such compounds/indicators.

In CSQD method embodiments, detecting the difference in the amount(s) of two or more compounds in samples from different parts of a site/area, or, also or alternatively, detecting the difference in the ratio(s) of two or more compounds in samples from different parts of a site/area, can be used to identify areas of significant interaction between rock and an associated fluid (e.g., oil). In aspects, the difference in the presence amount(s) of two such compounds between samples can predict or aid the prediction of the presence of fault(s) in both carbonate-rich and carbonate-poor (or carbonate-free) samples/formations. In aspects, the difference in the ratio of two such compounds between samples can predict or aid in the prediction of the presence of fault(s) or other conduits or conditions in both carbonate-rich and carbonate-poor (or carbonate-free) samples/formations.

According to certain aspects, exemplary oil compound indicators suitable for such a CSQD method analysis comprise two or more compounds wherein at least one compound of the at least two compounds is restricted in its ability to establish multiple conformations that significantly change the compound's size or shape. In aspects, such suitable compound(s) have a fixed or ridged structure regardless of encountered environmental temperatures. Skilled persons will have an understanding of rigid compounds in relevant materials, examples of which are described herein. In aspects, some, most, generally all, or all of such rigid compounds have a planar configuration, do not assume multiple configurations, have a simple chemical structure (e.g., comprise less than 8, less than 6, or less than 5 carbon atoms), contain one or more multiple bonds or aromatic rings, and the like. For example, a cyclohexane, which is well known to adopt different conformations (boat and chair conformations) may not be sufficiently rigid in certain aspects for use as an indicator compound. In aspects, compounds lacking such uniformity in size or shape across conditions, e.g., across varying temperatures, can be utilized in CSQD methods if a second compound is utilized comprising such uniformity in size or shape across conditions (e.g., across temperatures). In certain aspects, two compounds are suitable for use in CSQD methods herein if the two molecules cannot take on similar dimensions to one another such that the size of the molecules can become within about 15%, within about 14%, within about 13%, within about 12%, within about 11%, within about 10%, within about 9%, within about 8%, within about 7%, within about 6%, within about 5%, within about 4%, within about 3%, within about 2%, or, e.g., within about 1% of one another. Further discussion of such an exemplary characteristic of suitable compound(s) for use in CSQD method(s) is described below.

According to some aspects, exemplary oil compound indicators suitable for such a CSQD method analysis comprise two or more compounds where there is known relationship of what the ratio(s) between such indicator compounds is likely to be in an unfractionated system, rock formation, or the like, which is relevant to the analysis. For example, such data for several compounds can be found in, e.g., a commonly referenced paper in the art from 1968 by Harold M. Smith titled, "Qualitative and Quantitative Aspects of Crude Oil Composition" (Bulletin 642, Bureau of Mines, United States Department of the Interior) among other references known to those skilled in the art. In aspects, knowing the expected/known ratio(s) between the two or more compounds in a rock formation/area or unfractionated system (e.g., within common oils/gasses) provides a baseline against which obtained ratios can be compared to determine whether or not fractionation is likely to have occurred in the location from which analyzed samples were conducted, indicating fluid movement and, e.g., the presence of, or increased likelihood of the presence of, a fault. Exemplary oil compounds having such expected fixed relationships in unfractionated systems are, for example, toluene and benzene, methane, and propane, and, e.g., cyclopentane vs. methylcyclopentane. In aspects, two exemplary compounds which when used together would be unsuitable for use in the CSQD methods described herein are, e.g., 3-methylhexane and 2-methylhexane, 3-methylheptane and 2 methylheptane, toluene and methylcyclohexane, and toluene and n-heptane, and n-heptane and methylcyclohexane, as each show significant variation in respect to one another across produced crude oils. Typically, indicator compounds will (a) both be present in relevant amounts in petroleum products (e.g., be present typically at a level accounting for e.g., at least about 0.1%, at least about 0.25%, at least about 0.5%, at least about 0.75%, or at least about 1% of a petroleum composition), (b) will be compounds having rigid structures and/or having less than 2, less than 1, or no isomeric forms associated therewith, and (c) will have sufficiently different size, shape, or affinity characteristics, or a combination thereof, such that a detectable or significant amount of at least one of the indicator compounds will not travel as far as, in the same amount as, or both, as other indicator compound(s) analyzed, when conditions impacting petroleum migration are present (e.g., a fault or other conduit).

In aspects two or more such oil indicators can be compounds varying in size by about 10-50%, 10-100%, 10-200%, 10-500%, 20-100%, 20-60%, 20-200%, or 20-500%. In aspects, two or more of such oil indicator compounds can vary in weight by about 10-500%, e.g., 12.5%-250%, 12.5%-100%, or 12.5-50%, e.g., 15-150%, 15-90%, 15-45%, or 15-30%. In aspects, the molecular weight of a first oil indicator (e.g., oil indicator compound) compound is at least about 1.1 times, at least about 1.25 times, or at least about 1.5 times, 1.75 times, 2 times, 2.5 times, 3 times, 3.5 times, 4 times, 4.5 times, or even 5 times the molecular weight of a second oil indicator (e.g., about 1.1-2 times, about 1.1-1.5 times, or about 1.15-1.75 times).

In aspects, two or more such oil indicators can be compounds varying in their ability to move within a rock material such that within the same period of time and under the same conditions, a first compound is capable of moving at least about 5%, at least about 10%, at least about 20%, at least about 30%, at least about 40%, at least about 50%, at least about 60%, at least about 70%, at least about 80%, at least about 90%, or at least about 100% further or more (travel a distance about 5%, at least about 25%, at least about 50%, or at least about 100% further) than a second compound, or for example, is capable of moving at a speed which is at least about 5%, at least about 10%, at least about 20%, at least about 30%, at least about 40%, at least about 50%, at least about 60%, at least about 70%, at least about 80%, at least about 90%, or at least about 100% faster than that of a second compound. In aspects, the amount of one indicator that migrates from an area under a set of conditions (e.g., the presence of a fault) is at least about 5%, at least about 10%, at least about 20%, at least about 30%, at least about 50%, or at least about 75% less than the amount of another indicator compound that leaves the area under such conditions.

In certain aspects, two or more compounds suitable for use in this aspect of the invention can vary in size, weight, and or mobility through a rock material or any combination thereof. In some aspects, two or more compounds suitable for use in CSQD methods described herein are two or more compounds in which a) one compound has a relatively consistent size, shape, or size and shape across varying environmental temperatures (e.g., one compound of two compounds used in the analysis varies in size by no more than about 5%, no more than about 4%, no more than about 3%, no more than about 2%, no more than about 1%, or by no more than about 0.8%, no more than about 0.6%, no more than about 0.4%, or by no more than about 0.2% across varying temperatures); b) the two or more compounds have a relationship known in the art to be relatively consistent across crude samples (e.g., their relationship is accepted within the art to vary by no more than about 10%, no more than about 9%, no more than about 8%, no more than about 7%, no more than about 6%, no more than about 5%, no more than about 4%, no more than about 3%, no more than about 2%, or by no more than about 1% or less across varying crude samples); c) the two compounds vary in size such that their motility/mobility characteristics through a given rock are measurably different, or d) all of (a), (b), and (c) are true. In aspects, one or more such characteristics (a)-(c) can be missing yet the two or more compounds can be suitable for use within the CSQD methods herein, an example of which is methane and propane, methane and butane, and methane and pentane, wherein no known relatively fixed relationships between such compounds is readily accepted in the art, however other differences between the compounds can be sufficient for use in the CSQD methods herein whereby their use in such methods can result in identifiable features such as faults. In certain aspects, one or more compounds can be present in an amount which is significantly reduced from what would normally be expected or, for example can be absent when it would otherwise be expected, while other compounds can be present in expected amounts or a minimum present, and the difference in the presence of one compound and relative absence of another can be indicative of fractionation of the compounds even if ratios between such compounds are not established in the art as being relatively fixed. See, e.g., Example 5 described herein.

In aspects, exemplary oil compound indicators suitable for such a CSQD method analysis, including the ratios thereof, can be selected from a group comprising but not limited to methane, C2-C20, C4-C20, C2-C12, C3-C12, C4-C12, C4-C10, C2-C10, C3-C10, or C4-C10 compounds (for example, benzene and toluene), including, e.g., two or more paraffins, naphthenes, and aromatics. In aspects, some, most, generally all, or all of the indicator compounds used in a CSQD analysis differ from one another in structure by one or more atoms, typically one or more non-hydrogen atoms, and often one or more carbon atoms. Often, most, generally all, or all of the indicator compounds differ by only one or a few atoms, such as one or a few carbon atoms (e.g., 1-4, 1-3, or 1-2 carbon atoms). In certain particular aspects, two compounds suitable for such an analysis comprise benzene and toluene (e.g., a CSQD method comprises analyzing a toluene/benzene ratio for two or more sets of samples, sites, etc.). Applications of the analysis of toluene/benzene ratio(s) have been described in my previous work, specifically in PCT Application No. PCT/US19/22362, filed Mar. 14, 2019, and published Sep. 19, 2019 as WO2019/178418, and in U.S. patent application Ser. No. 17/019,130 filed Sep. 11, 2020 (a continuation of the PCT application). Methods described in this application can be combined with one or more aspects of the method(s) described in these applications.

In aspects, such differences in size, weight, or motility/mobility within rock between the two or more different indicator compounds analyzed in samples from different parts of a site/area in CSQD methods are sufficient to detectably or significantly cause differences in the amount of one or more of the compounds remaining in a location when oil-associated compounds migrate as compare to smaller and/or otherwise more mobile compounds (other indicators).

For example, toluene and benzene are two oil-associated compounds (and, thus, potential indicators) differing in size, with toluene being a larger molecule than benzene (by the addition of one carbon group attached to the benzene ring). When oil migrates, a detectably or significantly greater amount of toluene can be left behind in a site than benzene due to the greater size of toluene. An expected toluene: benzene ratio in a petroleum well site is, e.g., approximately 3:1. In aspects, the identification of a toluene:benzene ratio greater than that expected in a site can indicate the presence of a fault, other structure, or other condition/situation in which there has been a migration of oil from the site. For example, the identification of an area wherein the toluene: benzene ratio is at least approximately 3.4:1, about 3.5:1, about 3.6:1, about 3.7:1, about 3.8:1, about 3.9:1, about 4:1, about 4.25:1, about 4.5:1, about 5:1, about 5.5:1, about 6:1, about 6.5:1, about 7:1, about 8:1, about 9:1, about 10:1, about 12:1, about 14:1, about 16:1, about 18:1, or for example approximately 20:1 or more can indicate oil migration in/from such an area, identifying the presence of fault(s) or potential fault(s) in that area. Such a method is applicable to carbonate-rich rock and rock samples, carbonate-poor rock and rock samples, carbonate-rich formations, carbonate-poor formations, or, generally, carbonate-rich or carbonate poor materials). E.g., a ratio wherein a less mobile compound (indicator) is present in an amount which is at least about 10%, at least about 20%, at least about 30%, a least about 50%, at least about 75%, at least about 100% (i.e., 2×), at least about 150%, or at least about 200% higher that of the normal ratio for the relevant geologic formation/sample type can be indicative of the presence of a fault. In other aspects, such methods comprise direct comparison of indicators that differ in size from other indicators across different parts of a site/area or formation, with detectable or significant differences in the amount of an indicator (such as a percentage difference like any of those described above), being the basis for concluding that there is a fault, similar condition, or existence of a recent fluid migration event in the area (e.g., petroleum moving from one part of an area to another). In aspects, both relative measurements and measurements against expected standards are performed. Such standard ratios are known for many types of well characterized geologic formations. Other aspects of compound mobility also or alternatively can be the basis for selection of different indicator comparators, such as differences in compound affinities, differences in steric hindrance/size of compounds, and the like, provided such differences are detectably sufficient or significantly sufficient to often, usually, generally always, or essentially always identify/accurately predict differences in migration or conditions such as faults in a site, or other conduit for loss of pressure and fluid (e.g., nearby borehole(s)). Thus, while toluene and benzene are specifically exemplified here, this principle of indicator compound comparison can be extended to similar compounds measured by RVS methods having similarly known properties in terms of size, weight, and/or affinity or other chemical differences that would likewise indicate a correspondingly high proportion of less mobile compound indicator(s) to more mobile compound indicator(s) analyzed in the CSQD analysis, thereby indicating there has been interactions of large volumes of the compound-associated material of interest (e.g., oil), in the relevant zone, which provides an identification of a likely fault zone, similar structure, condition, or event (e.g., a migration of oil in the area).

As stated above, in aspects, suitable compounds for use in CSQD method(s) comprise at least one compound having a relatively uniform size and shape (e.g., in terms of conformation) across varying environmental conditions such as, e.g., temperature. The following table (Table 1) is provided to exemplify such a characteristic. Table 1 below (comprising values calculated based on models generated by the ChemDraw 3D program and presented in Smith, M; Smith, C. Advanced Geochemical Analysis of Volatiles Present in Drill Cuttings to Drive Decisions from Single Well Completions to Acreage/Basin Assessments: Examples from the Permian, STACK, and SCOOP in URTeC Conference Paper, Austin, 2020) illustrates the characteristics of Benzene, Toluene, and n-Decane relevant to structure that make Benzene and Toluene suitable compounds for use in CSQD methods described here, and making n-Decane a non-preferred compound, or a compound that, if utilized in a CSQD method, should be utilized in combination with a second compound demonstrating a uniformity more like that of Benzene or Toluene. As shown, Benzene and Toluene comprise both length and width measurements across a 132- degree Celsius temperature range (temperatures ranging from 25 degrees Celsius to 157 degrees Celsius) which vary by no more than 0.2% on average, wherein, n-Decane comprises length and width measurements across the same temperature ranges of at least 8% on average.

TABLE 1

Average length and width of Benzene, Toluene, and n-Decane Molecules by Temperature.

| Temp (C. °) | Benzene Length (Å) | Width (Å) | Toluene Length (Å) | Width (Å) | n-Decane Length (Å) | Width (Å) |
|---|---|---|---|---|---|---|
| 25 | 4.91 ± 0.025 | 4.26 ± 0.030 | 5.87 ± 0.052 | 4.5 ± 0.11 | 12.8 ± 0.92 | 3.8 ± 0.86 |
| 50 | 4.92 ± 0.024 | 4.27 ± 0.045 | — | — | 12 ± 1.4 | 4 ± 1.3 |
| 93 | 4.94 ± 0.031 | 4.28 ± 0.038 | 5.88 ± 0.053 | 4.51 ± 0.099 | 12.7 ± 0.96 | 3.9 ± 0.83 |
| 157 | 4.91 ± 0.027 | 4.27 ± 0.036 | 5.89 ± 0.053 | 4.5 ± 0.12 | 13 ± 0.53 | 3.6 ± 0.60 |

Therefore, in aspects, compounds suitable for use in CSQD methods can comprise at least one compound wherein the length of the compound, width of the compound, or both, do not vary, generally, at all, mostly, or on average, by more than about 1%, such as by no more than about 0.9%, about 0.8%, about 0.7%, about 0.6%, about 0.5%, about 0.4%, about 0.3%, about 0.2%, or by no more than about 0.1% or even less. In aspects, one or both dimensions of a compound used in CSQD analysis, most compounds used in the analysis, or all compounds used in the analysis exhibit such little variation (or no detectable variation) regardless of the environmental temperature in which the compound is located (e.g., between 25-157 degrees Celsius).

According to some aspects, the mechanical strength of collected samples can be measured in conjunction with any one or more methods described herein. In aspects, the mechanical strength of rock can be measured using techniques described in my earlier work cited herein (e.g., "frackability" methods described in my earlier-filed patent applications and patents). In aspects, mechanical strength data can be measured in conjunction with, e.g., LVCFI methods, and mechanical strength data can provide additional support for the identification of a fault within a sampled area (e.g., within a sampled well). In some aspects, the closer to a fault samples are collected, the lower the mechanical strength of the rock. In aspects, the mechanical strength of rock can increase as the distance away from the fault increases. Therefore, in aspects, when analyzing mechanical strength data, a decrease in mechanical strength data over a span of a well can indicate the approach toward a fault, and a subsequent increase in mechanical strength data can indicate moving away from the fault as the span of the well is traversed. In aspects, such principles can be applied to samples collected within a well or across multiple wells.

In aspects two or more such oil indicators can be compounds varying in size by about 10-50%, 10-100%, 10-200%, 10-500%, 20-100%, 20-60%, 20-200%, or 20-500%. In aspects, two or more of such oil indicator compounds can vary in weight by about 10-500%, e.g., 12.5%-250%, 12.5%-100%, or 12.5-50%, e.g., 15-150%, 15-90%, 15-45%, or 15-30%. In aspects, at least one molecular weight at least about 1.1 times, at least about 1.25 times, or at least about 1.5 times, 1.75 times, 2 times, 2.5 times, 3 times, 3.5 times, 4 times, 4.5 times, or even 5 times the molecular weight of a second oil indicator (e.g., about 1.1-2 times, about 1.1-1.5 times, or about 1.15-1.75 times).

In aspects, two or more such oil indicators can be compounds varying in their ability to move within a rock material such that within the same period of time and under the same conditions, a first compound is capable of moving at least about 5%, at least about 10%, at least about 20%, at least about 30%, at least about 40%, at least about 50%, at least about 60%, at least about 70%, at least about 80%, at least about 90%, or at least about 100% further or more (travel a distance about 5%, at least about 25%, at least about 50%, or at least about 100% further) than a second compound, or for example, is capable of moving at a speed which is at least about 5%, at least about 10%, at least about 20%, at least about 30%, at least about 40%, at least about 50%, at least about 60%, at least about 70%, at least about 80%, at least about 90%, or at least about 100% faster than that of a second compound. In aspects, the amount of one indicator that migrates from an area under a set of conditions (e.g., the presence of a fault) is at least about 5%, at least about 10%, at least about 20%, at least about 30%, at least about 50%, or at least about 75% less than the amount of another indicator compound that leaves the area under such conditions.

In certain aspects, two or more compounds suitable for use in this aspect of the invention can vary in size, weight, and or mobility through a rock material or any combination thereof.

Aspects of the invention whereby the analysis of two or more compounds varying in size, weight, and or mobility through a rock material are characterized such that the presence or likelihood of the presence of a fault (or other structure causing the loss or significant reduction in a compound) can be discerned is applied to a defined area, or relatively small zone of a geologic area, such as an area of about 200-about 1000 feet, such as about 300-about 900 feet, e.g., about 350-750 or about 350-700 feet, e.g., about 250-650, about 300-600, or about 350-550 feet. In aspects, significant differences between two or more oil indicators or ratios of indicators having, e.g., different size, weight, or mobility characteristics identified via RVS techniques, for example differences of at least about 1.5×, at least about 2×, at least about 3×, at least about 3.5×, at least about 4×, at least about 5×, at least about 10×, at least about 15×, at least about 20×, or more within a relatively narrow zone of a geologic area, e.g., within about 200-1000 feet, such as within about 250-about 800 feet, can be used to identify areas of significant interaction between rock and associated fluid (e.g. oil). In aspects, such differences can be used to predict faults in both carbonate-rich and carbonate-poor/carbonate-free samples/formations. The application of this embodiment of the invention is exemplified in Example 4.

In certain aspects, the invention provides a method of identifying a region of a geologic area that is likely to contain a fault comprising (a) subjecting a plurality of rock samples obtained from a plurality of separated sites in the area to one or more conditions that can cause the release of at least two rock volatile compounds from the samples, if present, wherein the at least two rock volatile compounds differ from one another by at least 20% in size, at least 20% in weight, at least 20% in their motility/mobility through the sampled rock, or any combination thereof, (b) measuring the amount of the two or more rock volatile compounds released from the rock samples, and (c) identifying regions in the area that are associated with differences in the amounts of the two or more rock volatile compounds or areas associated with differences in the ratios between the two or more rock volatile compounds. In certain aspects, the region of the geologic area is less than 1000 feet across in any one direction. In aspects, the results of such an analysis can be used to identify one or more areas containing or likely to contain a fault.

As noted above, the various analytical methods of the RVS applications can be applied to the analysis of $CO_2$-volatiles from rock samples, such as cuttings. Thus, for example, in one aspect the step of causing the release of $CO_2$-volatiles, if present, includes the method of subjecting samples to a vacuum, such as a gentle vacuum (e.g., pressure conditions of about 1 millibar to about 100 millibars, e.g., for a period ranging from about 0.15 minutes to about 15 minutes (such as 0.25 minutes to about 12 minutes, about 0.5 minutes to about 10 minutes, etc.). Typically, such a vacuum pressure is only applied once to the rock samples to release volatile compounds, if present, such as $CO_2$-volatiles, if present.

The measurement of carbon dioxide and or CDRCs ($CO_2$-volatiles), in such aspects of the invention also or alternatively can comprise the step of (a) trapping gas released from the rock samples with a trap capable of selectively releasably binding the carbon dioxide, carbon dioxide-related compound, or combination thereof, (b) releasing the gas from the trap, and (c) subjecting the gas to chemical analysis, typically comprising mass spectrometry analysis. The selective release means that the release of gas can be triggered by change of conditions, such as increasing the heat in a system comprising a cryogenic gas trap, as described in the RVS applications. Typically, a trap used in such aspects of the invention is non-selective in terms of any specific type of compound, thus allowing several types of $CO_2$-volatiles to bind the trap. In other aspects, trapping methods that are specific for one or more $CO_2$-volatiles can be used.

As noted above, methods of the invention can include collecting samples in a sample container such as described in the RVS applications. Thus, in one facet, a method of the invention can further comprise the steps of (a) placing the rock sample in a crushable and selectively traversable container that is capable of being mechanically crushed without releasing volatiles prior to releasing the carbon dioxide, carbon dioxide-related compound, or a combination thereof, (b) crushing the container, and (c) traversing the container with a device or component that allows gas to flow from the interior of the container for analysis of the amount of carbon dioxide, carbon dioxide-related compound, or a combination thereof in the gas, wherein the amount of crushing of the container corresponds to the strength of the rock sample. In another aspect, the inventive method is combined also or alternatively with performing a permeability analysis of the rocks, as described in the RVS applications.

In aspects, one or more computers or computer-associated components (e.g., software, data processor(s), data repository(ies), visual presentation component(s) such as, e.g., a monitor or other user interface, or the like) can be utilized in any method described here to aid in or otherwise direct the operation of analytical equipment, to collect, compile, compare, process, store, present, or manipulate data to facilitate the application of the methods herein, or to otherwise interpret the data resulting therefrom.

For example, in aspects, a method described herein can comprise use of a computer processing system to analyze, process, or interpret $CO_2$-content data to identify positional characteristics of rock samples, e.g., differences in $CO_2$-content data from location to location (e.g., differences in $CO_2$-content data across samples collected from different locations within the same borehole). In alternative aspects, use of a computer processing system can be applied to the analysis of $CO_2$-content data collected on samples of carbonate rock(s) from boreholes drilled using the same or comparable drilling techniques to identify differences in $CO_2$-content data across a plurality of boreholes. In aspects, computer processing systems can comprise software allowing for such systems to analyze one or more data sets and generate one or more maps (e.g., geological maps), graphs, charts, or other visual representations, interpretations, or presentations of the data.

In aspects, use of such computer systems, computer-related components, or otherwise automated methods can provide maps of the geological areas from which samples are collected and analyzed, such as, e.g., samples collected from within a single borehole or from a plurality of boreholes within an area, such maps characterizing the geological site or area based upon the results of the methods described herein.

In certain aspects, methods described here can comprise use of one or more computer systems or computer-associated components which can assign a rock type identifier to one or more samples based on the results of CDRC/$CO_2$-volatiles analysis (e.g., can identify a rock sample as a Type I or Type II rock). In aspects, CDRC/$CO_2$ methods can comprise analyzing the predicted coarseness resulting from the $CO_2$ or CDRC data using automated methods (e.g., one or more computer-associated components such as a data processor) and generating a map of the coarseness-results by the physical location from which the samples were collected to provide a map of the carbonate grain size of materials within areas of the geologic site/area analyzed. In certain embodiments, the method comprises generating a physical map of a single borehole. In certain alternative embodiments, the method comprises generating a physical map of a region. In some embodiments, the map is a digital map or plot of the region reflecting the carbonate grain size of the carbonate rock-containing structures in the region, and optionally the presence of suspected faults based on other aspects of the inventive method described further herein.

In embodiments, methods herein can comprise use of one or more computer systems or computer-associated components which can compile data from the methods described here (e.g., CDRC/$CO_2$-volatiles analysis data, CSQD analysis data, or LVCFI analysis data) with data collected using one or more other technologies, e.g., gamma ray analysis data or other data collected or analyzed separately from the methods here. In aspects, the combination of such data can improve upon the detail or insight provided by the analysis or presentation of CDRC/$CO_2$-volatiles analysis data or CSQD analysis data alone.

In aspects, the invention provides a computer comprising computer readable media comprising instructions for performing any one or more of the analytical methods described herein (e.g., a CSQD analysis or a carbon-dioxide or carbon dioxide-related compound analysis, or a lack of carbon dioxide analysis), optionally in combination with consideration of other data (e.g., standards, compound measurements, and the like, e.g., obtained by rock volatiles stratigraphy, fluid inclusion analysis, conventional well logs, and/or gamma ray analysis) and processors for performing such analysis, along with relevant forms of output (e.g., graphical user interface outputs, and the like). In aspects, such computer systems control the operation of other devices, such as other computer user interfaces or control over devices involved in petroleum production, such as in directing drilling of a petroleum site, fracking operations, or controlling other physical operations in petroleum production (e.g., guiding devices or processes in production).

In aspects, where samples are collected from boreholes drilled using different technologies or techniques whereby such differences prevent the direct comparison of data resulting from the analysis of such samples, one or more computer-related systems can be utilized to automatically generate and apply an appropriate scaling factor to one or more data points (such scaling factors described elsewhere here) to facilitate the comparison of the samples and any accompanying interpretation and presentation of such results. In aspects, such a comparison can occur automatically upon the application of applicable scaling factors.

In another aspect, any of the various steps described herein (e.g., extraction of volatiles, collection of mechanical strength, and the like) are under the control of a computer operating on preprogrammed instructions according to one or more principles of the invention described herein.

It should be clearly stated that when describing an application of an inventive method, such an inventive method can in aspects apply to any suitable method herein, such as CDRC/$CO_2$ method(s), CSQD method(s), LVCFI method(s), and the collection and analysis of mechanical strength data. In particular aspects, CDRC/$CO_2$ methods and LVCFI method(s) may be beneficially performed or utilized together, such that $CO_2$/CDRC analysis results can be utilized both to predict grain size and associated predictive petroleum productivity as well as to identify the presence of, or the increased likelihood of the presence of, a fault.

As previously described, in aspects the methods of the invention provide a number of advantages for those applying these methods to characterize geologic areas, such as petroleum exploration and/or production sites. In aspects, the inventive method provides geologists and technicians with the ability to obtain gamma ray-like results from carbonate rocks, thus providing a more complete picture of the geology of regions, which previously was limited to clastic-dominated regions. In certain aspects, the techniques of the invention are also particularly needed in current (at the time of this application) drilling environment(s) where the use of Polycrystalline Diamond Compact (PDC) bits results in cuttings commonly less than a millimeter in their largest dimension, and thus making it difficult to discern the carbonates rock type from the cuttings samples. The technique is also particularly useful, in aspects, for well site operations, and rapid laboratory operations, as it can provide data quickly in a time frame that allows those data to be used in an operation sense, such as picking a landing zone for a horizontal well from a vertical pilot hole, or helping design how a well will be completed, such as stage placement and fracking intensity in a horizontal well. Finally, it is again worth noting that the techniques of the invention can be applied to old or new cuttings, from PDC bit or rock bit drilled cuttings, and from either wells drilled using Water Based Muds (WBM) or Oil Based Muds (OBM).

EXAMPLES

The following Examples are provided to illustrate exemplary concepts and practices relevant to the practice of the inventive methods provided herein. The breadth and scope of the present invention should not be limited by any of the following exemplary embodiments; but should be defined only in accordance with the following claims and their equivalents.

Example 1

Samples of PDC drill cuttings were collected from a drilling site (WELL 1) representative of the rock composition across the depths of the well, cuttings being sub-millimeter in size. Sample cuttings were gently caught then washed. Grain size of cuttings were characterized according to known techniques and recorded for each sample. Samples were characterized for the purposes of this method as Type I or Type II according to grain size, Type I being large or coarse grain size, Type II being small or fine grain size. Samples were then tested for volatiles using mass spectrometry analysis methods previously described in the RVS applications. Such volatiles analysis included analysis of $CO_2$ and CDRCs released by the sample cuttings upon crushing as part of the method described herein. $CO_2$ results of cuttings across the depths of the well were then compiled into a single visual analysis, plotting the $CO_2$ released by cuttings collected at the varying depths of the well on a graph of FIG. 1 (and repeated in 3A). In FIG. 1, the scale at the top of the Figure is the mass spec response (digitized voltage signal); the scale on the left of the graph is the well depth (in feet. In combination with the known grain size of the cuttings, $CO_2$ results, as demonstrated in FIG. 1, demonstrate that it is possible to distinguish between different rock types, as indicated by differences in the amount of $CO_2$ released during volatiles analysis. This data, in combination with secondary analysis of grain composition and characterization of cuttings into Type I and Type II rock according to grain size, indicates that $CO_2$ as measured via the mass spectrophotometric analysis method is correlated with grain size.

Example 2

Samples of PDC drill cuttings were collected from a drilling site (WELL 2) representative of the rock composition across the depths of the well. Cuttings were on average sub-millimeter in size. Sample cuttings were gently caught then washed. Grain size of cuttings were characterized according to known techniques and recorded for each sample. Samples were characterized for the purposes of this method as Type I or Type II according to grain size, Type I being large or coarse grain size, Type II being small or fine grain size. Samples were then tested for volatiles using mass spectrometry analysis methods previously described. Such volatiles analysis included analysis of $CO_2$ and CDRCs released by the sample cuttings upon crushing as part of the method described herein. $CO_2$ results of cuttings across the depths of the well were then compiled into a single visual analysis, plotting the $CO_2$ released by cuttings collected at the varying depths of the well on a graph (FIG. 3B). In combination with the known grain size of the cuttings, $CO_2$ results demonstrate that it is possible to distinguish between different rock types, as indicated by differences in the amount of $CO_2$ released during volatiles analysis. This data, in combination with secondary analysis of grain composition and characterization of cuttings into Type I and Type II rock according to grain size, indicates that $CO_2$ as measured via the mass spectrophotometric analysis method is correlated with grain size. The data from EXAMPLE 1 is shown in FIG. 1 and FIG. 3a. The data from EXAMPLE 2 is shown in FIG. 3b. FIG. 3 shows EXAMPLE 1 and EXAMPLE 2 data side by side, illustrating repeatability of the method and its ability to distinguish differences in rock types. Note that differences between the well in EXAMPLE 1 and EXAMPLE 2 include total well depth; Well 2 being over 1000 feet deeper than Well 1; and the well depths at which each rock type, Type I and Type II, are found. Such a comparison may be used in decision making related to which sites to pursue, as depth of particular rock types may drive decisions such as, for example, drilling costs and related return.

Example 3

Figure 4:
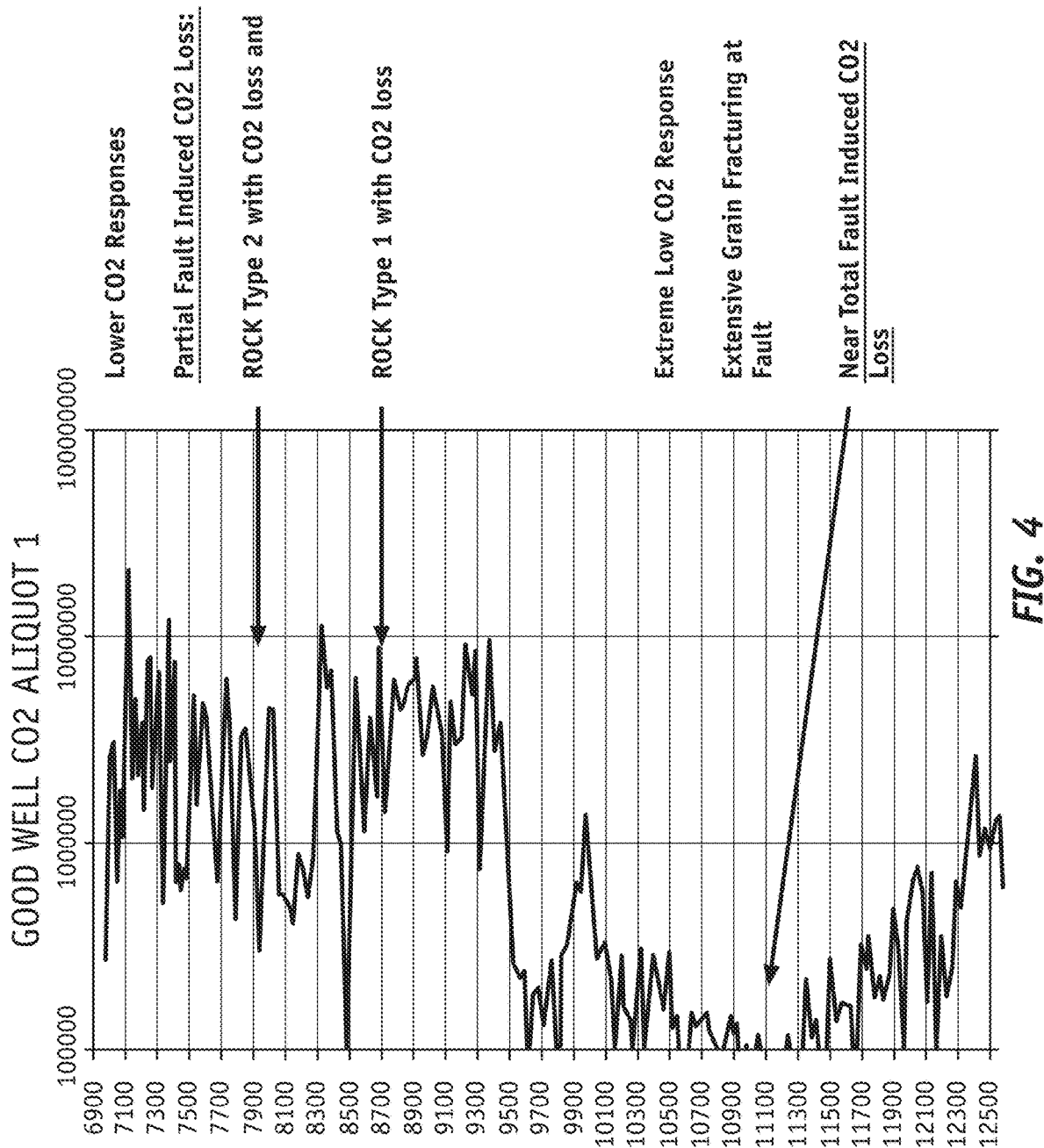
Figures 5, 5A, 5B:
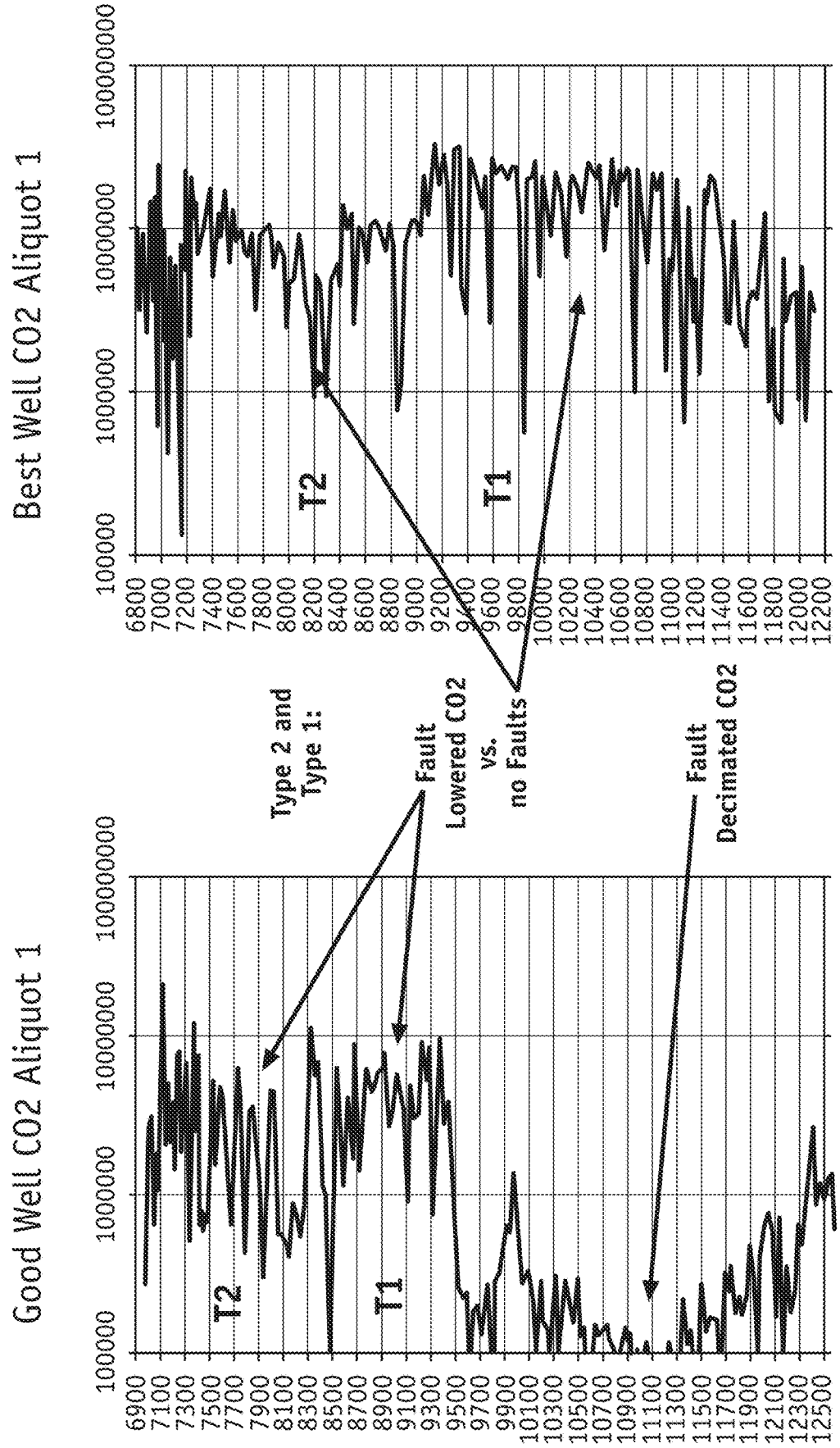

Samples of PDC drill cuttings were collected from a drilling site (WELL 3), a site geologically known to contain a fault and partial fault, the samples being representative of the rock composition across the depths of the well. Cuttings were sub-millimeter in size. Sample cuttings were gently caught then washed. Grain size of cuttings were characterized according to known techniques and recorded for each sample. Samples were characterized for the purposes of this method as Type I or Type II according to grain size, Type I being large or coarse grain size, Type II being small or fine grain size. Samples were then tested for volatiles using mass spectrometry analysis methods previously described. Such volatiles analysis included analysis of $CO_2$ and CDRCs released by the sample cuttings upon crushing as part of the method described herein. $CO_2$ analysis results of cuttings across the depths of the well were then compiled into a single visual analysis, plotting the $CO_2$ released by cuttings collected at the varying depths of the well on a graph (FIG. 4). In combination with the known grain size of the cuttings, $CO_2$ results demonstrate that when $CO_2$ levels are low, it is difficult to distinguish between different types of rock. This occurs in areas where a partial fault is present. In this example, both rock Type 1 and rock Type II have experienced significant $CO_2$ loss and are therefore no longer distinguishable via the present method. Further, extremely low $CO_2$ is demonstrated by the present method in areas where extensive grain fracturing has occurred in the rock samples at a fault, where near total fault-induced $CO_2$ loss has occurred. This data, presented in FIG. 4, illustrates that a partial fault is present at more shallow depths of the well, a location where distinction between Type I and Type II rocks cannot be made due to significant $CO_2$ loss. At deeper areas of the well, closest to the fault, extreme low $CO_2$ response is observed. Such observations of extreme low $CO_2$ may be correlated with extensive grain fracturing and therefore low amounts of fluid inclusions, cracks, or other structures that in otherwise e similar, non-fault associated rocks, contain relatively higher amounts of $CO_2$-volatiles.

Example 4

Figure 6:
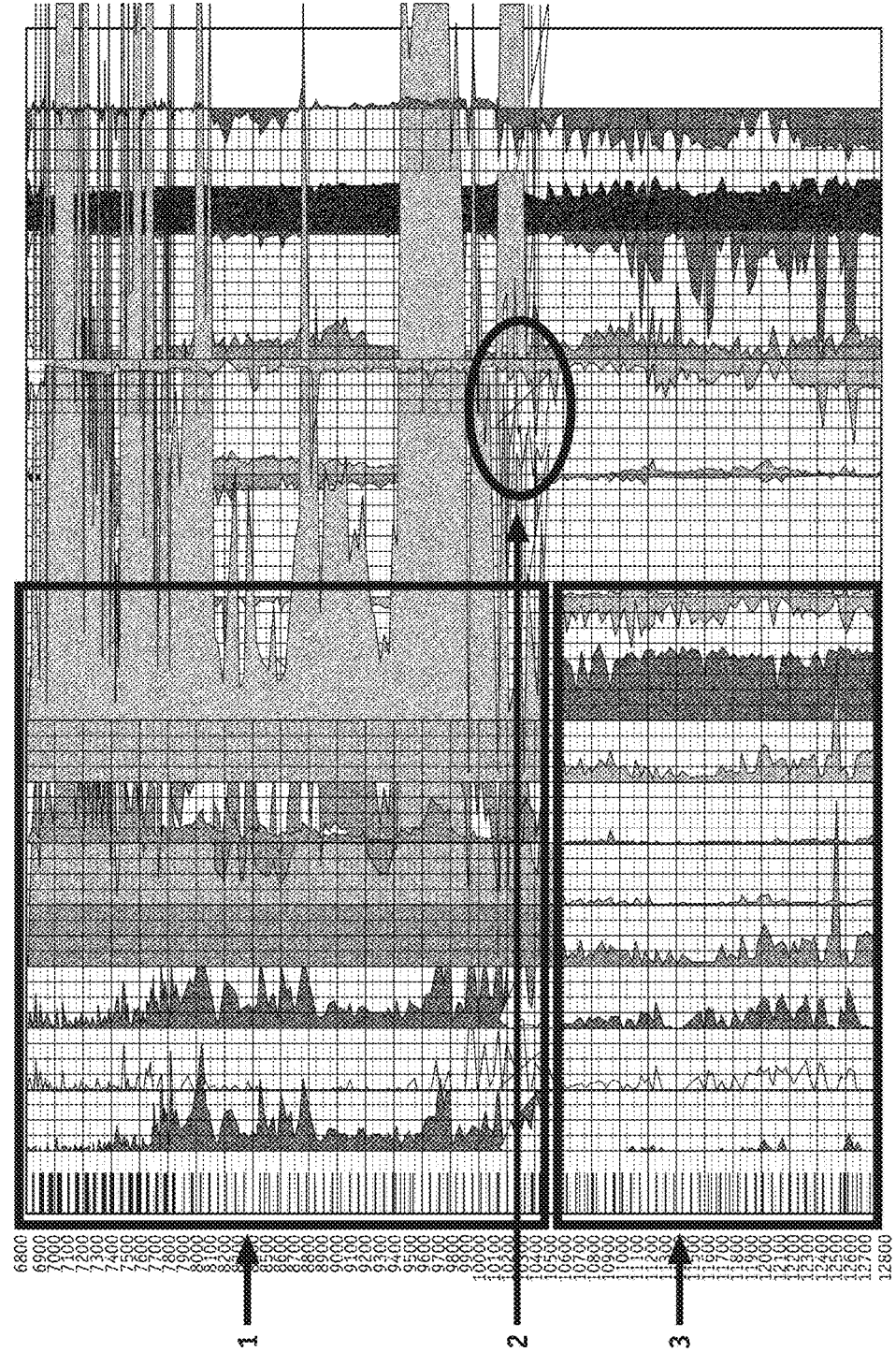
FIG. 6 is a graph of the content of various compounds obtained by application of RVS technology on a well containing a fault, exemplifying another aspect of the invention, specifically how differences in rock-associated compound content can also or alternatively be used to identify fault structures in a geologic formation, in both carbonate and non-carbonate rocks.

RVS was performed using numerous conventional petroleum drill cutting samples collected from a lateral horizontal oil well using the methods described in detail in the RVS applications incorporated herein by reference using a number of target compounds identified from rocks that were not limited to or even predominately made up of carbonate materials. The results of the investigation are shown in FIG. 6. Data associated with samples in the "heel" of the well are shown at the top of FIG. 6 and data associated with samples in the "toe" of the well are located near the bottom of FIG. 6.

As can be seen in FIG. 6, reference #1 reflects an area where more condensed, less fractured, and/or less permeable ("tighter") rocks were identified between oil rich zones, even though some indicators suggested that these rocks were also oil rich. This data reflects the fact that tighter rocks can often better maintain oil and gas from cuttings during drilling and transport of cuttings to the surface (before analysis).

The data associated with reference #2, reflect a zone of high toluene/benzene ratio is present at the expected fault, reflecting a zone of oil migration. Toluene is a larger molecule than benzene, and as such, more toluene is left behind during migration then benzene. The use of such a high toluene/benzene ratio (at least about 3.5:1, such as at least about 3.75:1, at least about 4:1, at least about 4.25:1, at least about 4.5:1, at least about 5:1, at least about 7:1, at least about 10:1, at least about 20:1 or more) to identify potential faults is one aspect of the invention (whether in carbonate rich or carbonate poor samples, carbonate poor formations, or, generally, carbonate poor materials). In this respect it is noted that a ratio of at least about 3.5:1 is greater than the typical toluene:benzene ratio in petroleum well sites of about 3:1, reflecting a greater than normal ratio (e.g., a ratio where the less mobile compound is present in at least about 10%, at least about 20%, at least about 30%, a least about 50%, at least about 75%, at least about 100% (i.e., 2×), at least about 150%, or at least about 200% that of the normal ratio for the relevant geologic formation/sample type. However, this principle can be extended to similar compounds measured by RVS methods having similarly known properties in terms of size, weight, and/or affinity or other chemical differences that would likewise indicate a correspondingly high proportion of a/the less mobile compound to a/the more mobile compound, thereby indicating there has been interactions of large volumes of the compound-associated material of interest (e.g., oil), in the relevant zone, which provides an identification of a likely fault zone.

The area associated with reference #3 of FIG. 6 reflects a predicted preferred reservoir zone using a combination of RVS data, despite the relatively lower total oil volume measures associated with the samples. This RVS data corresponded well with other analytical data (not shown) obtained by independent analysis using other reliable (albeit more expensive and/or sometimes limited) methods and revealed only after the reporting of the RVS data.

"Frackability" (mechanical strength) data obtained by other methods in the RVS applications reported below the identified fault zone (#3) with relatively low oil content indicators in some respects reflects the fact that high porosity and/or high permeability rocks can lose oil during drilling, transport, and analysis (e.g., sample preparation). This data reflects how RVS analysis can be used to better characterize petroleum properties than other methods given the multi-dimensional approach of RVS methods. Because of the relative compartmentalization of the oil below the predicted fault it is expected that the predicted preferred zone will produce oil more economically than the tight rock area associated with high total oil measurements.

This Example generally demonstrates how significant differences between two or more oil indicators having, e.g., different size, weight, or mobility characteristics identified via RVS techniques in a relatively narrow zone of a geologic sample can be used to identify areas of significant interaction between rock and associated fluid (e.g., oil) and also to predict faults in both carbonate-rich and carbonate-poor/carbonate-free samples/formations.

Example 5

Samples were collected from a gas well within the Marcellus Play (Pennsylvania, USA). Samples were collected approximately every 60 feet across a span of approximately 8000 feet. Rock volatile stratigraphy (RVS) analysis as described and referenced herein was performed on the collected samples and analyzed for the presence of methane, propane, butane, and pentane. Mechanical strength data measured using techniques described in my prior RVS work referenced herein also was collected for a representative number of samples such that the mechanical strength of rock across the span of the well could be established.

The results of volatiles analysis of methane-pentane (C1-C5 compounds) released from samples were plotted along with the mechanical strength data across the span of the well. Available LWD (logging while drilling) gamma ray log data also were plotted with the volatiles. Mechanical strength data associated with samples also was plotted. The gamma ray log data had previously indicated the possible existence of a fault at a well depth of between about 4500 and 5000 feet.

When comparing the volatiles data with the gamma log data, methane was shown to be almost immeasurable, e.g., effectively, absent over a span of 400-500 feet at a depth of about 4100 feet to about 4500 feet, wherein over that same 400-500-foot span, propane, butane, and pentane were all present.

While recognized ratios between methane and propane, methane and butane, and methane and pentane are not known to exist across crudes, the relative absence of methane in the presence of other compounds confirmed gamma ray log data that a fault existed, or confirmed the likelihood of a fault to exist, at that location within the well. Further, mechanical strength data, when analyzed in conjunction with the volatiles data, indicated a drop in mechanical strength in rock approaching the location of the drop in/absence of methane. This, too, supported the conclusion that a fault was present, at that location, or at a minimum, the likelihood of a fault being present at that location was increased. Weak mechanical strength and a loss of methane several hundred feet before a fault indicated by gamma ray data offered further evidence of the fault when combined with the LWD gamma ray data. The fault appeared to be providing a conductive pathway for methane to escape, but other molecules such as propane, butane, and pentane were too large to escape the rock. Yet further, additional analysis performed in conjunction with the analysis of the volatiles described above indicated that at the location within the well wherein gamma ray data and LVFIC methods indicated the presence of a fault, the water content of samples on the toe-side of the fault was significantly higher than the water content of samples on the heel-side of the fault, indicating, again, not only the presence or increased likelihood of the presence of a fault at the identified location, but also that the fault was playing a role in water distribution within the borehole. This Example exemplifies how methods of the invention can be used to identify the presence of geologic conditions in a geologic area such as the presence of a fault, conduit, or similar condition.

What is claimed is:

1. A method of estimating the carbonate grain size of a carbonate rock sample comprising (a) obtaining a carbonate rock sample from a geologic area expected or known to contain carbonate rocks; (b) subjecting the carbonate rock sample to conditions that will cause the release of a detectable amount of carbon dioxide, one or more carbon dioxide-related compounds, or a combination thereof from the rock sample, if present, (c) measuring the amount of carbon dioxide, one or more carbon dioxide-related compounds, or a combination thereof released from the carbonate rock sample, and (d) estimating the carbonate grain size of the carbonate rock sample by measuring the amount of the carbon dioxide, the one or more carbon dioxide-related compounds, or a combination thereof released from the rock sample, wherein less than about 5% of the carbon dioxide, the carbon dioxide-related compounds, or both, originate from carbonate material within the crystalline structure of the carbonate rock.

2. The method of claim 1, wherein the method is performed on multiple rock samples obtained from at least two regions of the geologic area that are at least 100 feet apart in at least one direction.

3. The method of claim 2, wherein the method is performed on at least 10 rock samples that are sourced from regions of the geologic area that are at least 100 feet apart in at least one direction from all the other samples.

4. The method of claim 3, wherein the rock samples are petroleum drill cuttings.

5. The method of claim 4, wherein step (b) of the method comprises physically disrupting the rock sample.

6. The method of claim 5, wherein at least 20% of the petroleum drill cuttings are Polycrystalline Diamond bit cuttings.

7. The method of claim 4, wherein the results obtained by performing the method are combined with the results of gamma ray analysis of rock samples from the geologic area to further characterize the geologic nature of the geologic area.

8. The method of claim 4, wherein the results obtained by performing the method are compared to or combined with the results of petroleum well logging to characterize the geologic nature of the geologic area.

9. The method of claim 4, wherein the results obtained by performing the method are combined with the results of rock volatiles analysis to characterize the geologic nature of the geologic area.

10. The method of claim 4, wherein the results of the method are used to select a location for drilling or extending a horizontal petroleum well.

11. The method of claim 4, wherein the results of the method are used to select a location for fracking operations.

12. The method of claim 4, wherein the method comprises identifying one or more regions in the geologic area that primarily comprise carbonate rocks but are associated with samples that release relatively low amounts of carbon dioxide, one or more carbon dioxide-related compounds, or both, wherein such regions are predictive of the presence of a fault in one or more regions, another type of conduit in the one or more regions, petroleum migration in the one or more regions, or a combination of any or all thereof.

13. The method of claim 4, wherein step (b) of the method comprises subjecting the rock sample to a pressure of about 1 millibar to about 100 millibars for a period ranging from about 0.15 minutes to about 15 minutes.

14. The method of claim 4, wherein the step of measuring the carbon dioxide, the one or more carbon dioxide-related compounds, or a combination thereof comprises (a) trapping gas released from the rock samples with a trap capable of selectively releasably binding the carbon dioxide, the one or more carbon dioxide-related compounds, or a combination of any or all thereof, (b) releasing the gas from the trap, and (c) subjecting the gas to mass spectrometry analysis.

15. The method of claim 4, wherein carbonate grain size analysis is performed on carbonate rocks obtained from a plurality of wells drilled using different drilling technologies or practices, and further wherein to facilitate the comparison of results, a scaling factor is applied to one or more results.

16. The method of claim 15, wherein the method comprises generating local and regional maps of carbonate grain size, $CO_2$ loss, or both, based on the results of the method.

* * * * *